US010001491B2

(12) United States Patent
Azria et al.

(10) Patent No.: US 10,001,491 B2
(45) Date of Patent: Jun. 19, 2018

(54) METHOD FOR DETERMINING RADIOSENSITIVITY

(71) Applicants: Centre Hospitalier Universitaire de Montpellier, Montpellier (FR); Universite de Montpellier, Montpellier (FR); Institut Regional du Cancer de Montpellier, Montpellier (FR)

(72) Inventors: David Azria, Fontanes (FR); Jerome Lacombe, Saint Gely du Fesc (FR); Jerome Solassol, Montpellier (FR); Alain Mange, Montpellier (FR)

(73) Assignees: Centre Hospitalier Universitaire de Montpellier (FR); Universite de Montpellier (FR); Institut Regional du Cancer de Montpellier (FR)

( * ) Notice: Subject to any disclaimer, the term of this patent is extended or adjusted under 35 U.S.C. 154(b) by 119 days.

(21) Appl. No.: 14/780,789

(22) PCT Filed: Mar. 28, 2014

(86) PCT No.: PCT/EP2014/056265
§ 371 (c)(1),
(2) Date: Sep. 28, 2015

(87) PCT Pub. No.: WO2014/154854
PCT Pub. Date: Oct. 2, 2014

(65) Prior Publication Data
US 2016/0054337 A1 Feb. 25, 2016

(30) Foreign Application Priority Data

Mar. 28, 2013 (EP) ..................................... 13305399

(51) Int. Cl.
*G01N 33/68* (2006.01)
*A61N 5/10* (2006.01)

(52) U.S. Cl.
CPC .......... *G01N 33/6893* (2013.01); *A61N 5/103* (2013.01); *G01N 2800/40* (2013.01); *G01N 2800/50* (2013.01); *G01N 2800/60* (2013.01); *G01N 2800/7004* (2013.01)

(58) Field of Classification Search
CPC ................................................ G01N 33/6893
See application file for complete search history.

(56) References Cited

U.S. PATENT DOCUMENTS

2013/0052668 A1\* 2/2013 Paulovich .......... G01N 33/6893
435/7.92

FOREIGN PATENT DOCUMENTS

WO 2013001507 A2 1/2013

OTHER PUBLICATIONS

Manzanares-Acuna et al. 2002; Cellular response to low gamma-ray doses. On the web at iaea.org/inis/NCLCollectionStore/_Public/34/023/34023868.pdf.*
International Search Report and Written Opinion issued in corresponding International Application No. PCT/EP2014/056265, dated Jun. 18, 2014.
Cai, et al. "Baseline Plasma Proteomic Analysis to Identify Biomarkers that Predict Radiation-Induced Lung Toxicity in Patients Receiving Radiation for Non-small Cell Lung Cancer", Journal of Thoracic Oncology: Official Publication of the International Association for the Study of Lung Cancer. vol. 6, No. 6, Jun. 2011. pp. 1073-1078.
Skvortsova, et al. "Intracellular signaling pathways regulating radioresistance of human prostate carcinoma cells" Proteomics vol. 8, No. 21, Nov. 2008, 4521-4533.
Stenmark et al. "Combining Physical and BioLogic Parameters to Predict Radiation-Induced Lung Toxicity in Patients With Non-Small-Cell Lung Cancer Treated With Definitive Radiation Therapy", International Journal of Radiation Oncology, Biology, Physics, Oct. 1, 20012. vol. 84, No. 2, 2012. pp. e217-e222.

\* cited by examiner

*Primary Examiner* — Karen Cochrane Carlson
(74) *Attorney, Agent, or Firm* — Banner & Witcoff, Ltd.

(57) ABSTRACT

The present invention relates to a method for the in vitro determination of the radiosensitivity of a subject. More particularly, the invention relates to a method comprising a step of inducing an exogenous stress on a biological sample from a subject, followed by the comparison of the presence or level of at least one compound chosen in a group of defined compounds, in said biological sample and in a reference sample. The present invention also relates to the use of said at least one compound as predictive biomarker of the radio-sensitivity of a subject. The invention also relates to a kit for the detection of the presence or level of at least one of said compounds, usable in a method according to the invention.

10 Claims, 4 Drawing Sheets

METHOD FOR DETERMINING RADIOSENSITIVITY

RELATED APPLICATION DATA

This application is a National Stage Application under 35 U.S.C. 371 of co-pending PCT application number PCT/EP2014/056265 designating the United States and filed Mar. 28, 2014; which claims the benefit of EP application number 13305399.1 and filed Mar. 28, 2013 each of which are hereby incorporated by reference in their entireties.

The present invention relates to a method for the in vitro determination of the radiosensitivity of a subject. More particularly, the invention relates to a method comprising the induction of an exogenous stress on a biological sample from a subject and the comparison of the level of at least one identified compound between said biological sample and a reference sample. The present invention also relates to the use of said at least one compound as a predictive biomarker of the radiosensitivity of a subject. The invention also relates to kit, usable in a method according to the invention, for the detection of the level of at least one of said identified compounds.

The success of radiotherapy mainly depends on the total administered dose. Individuals vary widely in the susceptibility of the tissue to ionizing radiation damage. Each year, about 4 million of people are treated by radiotherapy worldwide. Current estimates suggest that 5-10% of patients receiving radiotherapy display adverse reaction due to hypersensitivity. Patients hypersensitive to ionizing radiations may develop important radiation-induced side effect. The prediction of these side effects remains currently impossible, involving limiting the given dose with the risk to decrease the therapeutic benefit for patients. Laboratory methods for assessing radiosensitivity were, until now, too laborious for large populations to be examined.

A few tests for predicting radiotoxicity have been developed, however so far, none of them is usable in clinical routine.

A clonogenic test evaluates the loss of the ability of proliferation of lymphocytes after irradiation (West et al., 1995). Other tests are based on the detection of micronucleus after irradiation (Floyd and Cassoni, 1994). However, the routine implementation of these tests is limited and none of them are used clinically.

The radiation-induced lymphocyte apoptosis (RILA) assay measures the apoptosis in CD4 and CD8 T-lymphocytes after irradiation (0.5-8 Gy) via flow cytometry (Ozsahin et al., 1997, Azria et al., 2009). Results were confirmed on a cohort of 399 patients (Ozsahin et al., 2005). This measure is based on the decrease in nuclear DNA fluorescence due to specific chromatin changes that accompany apoptosis and is capable to identify hypersensitive patients. The positive predictive value of the RILA assay is weak, with 80% of patients of the population detected with a weak apoptosis level which do not present any late toxicity. The RILA assay has sensitivity of 0.70 and a specificity of inferior to 0.50 (Ozsahin et al., 2005).

A correlation between some genetic variations, such as Single Nucleotide Polymorphism (SNP), Copy Number Variability (CNV) or epigenetic modifications, and radiotoxicity has been studied (Azria et al., 2008, Azria et al., 2012). Some genes linked with DNA repair during oxidative stress or in inflammation have been identified and associated with early or late toxicity. However, until now, no link between genotype and radiotoxicity and no strong genetic marker of radiotoxicity have been shown.

Some proteomic studies have tentatively addressed the determination of radiosensitive markers. WO 2013/001507 describes a method including creating or adapting a treatment plan for a patient submitted to radiotherapy, wherein said method is based on a set of serum polypeptides of the patient that are indicative of a radiotoxicity. Alpha 1 anti-trypsin, APOA1 and complement C3 were found upregulated in serum of a mouse model exposed to ionising radiation (Guipaud et al., 2007). Cai et al. (2011) discloses a proteomic analysis of patients receiving radiation for non-small cell lung cancer. Complement C3, C4b-binding protein alpha chain and vitronectin were also found upregulated in a small cohort of radiation-induced lung toxicity grade >2 patients (Cai et al., 2010; Cai et al., 2011). Skvortsova et al. (2008) discloses the proteome profile of prostate carcinoma cell lines and of radiation-resistant prostate cancer cell lines. Stenmark et al. (2011) discloses circulating cytokine levels of patients receiving radiation therapy. Finally, Oh et al. proposed an original in silico analyses and identified α-2-macroglobulin as potentially associated with increased risk of radiation-induced lung inflammation in lung cancer patients but did not validated this results in an independent cohort (Oh et al., 2011).

None of the existing predictive test for radiosensitivity is usable in clinical routine, due to two major drawbacks: i) their lack of sensitivity and/or specificity, none having both good enough positive and negative predictive value, ii) their lack of technical feasibility and requirement of long delays, of highly trained practitioners, their high cost and the invasive collection of biological samples.

Therefore, there is still a need for simple, rapid and reliable method exhibiting a high positive and negative predictive value of radiosensitivity of a subject.

The inventors have shown that, upon induction of an exogenous stress on a biological sample from a subject or a patient, the determination of at least one of the identified differentially expressed compound reflects the radiosensitivity of said subject or patient. Therefore, this test allows the prediction of late radio-induced toxicity.

A method and a use according to the invention provide the physician with details of tissue radiosensitivity, and thus help the early recognition and appropriate handling of these hypersensitive patients. In addition, such method or assay could increase the total radiation dose for the majority of patients who are predicted not to be hypersensitive and possibly obtain a higher cure or control rate in these patients. On theoretical grounds, local tumor control could be significantly improved in a number of patients by moderately increasing the total radiation dose. It has been suggested that a 20% increase in control rates is feasible.

The present invention discloses a method which confirms results from the RILA assay and has a higher positive predictability. Furthermore, said method according to the invention can be used as a combination with other tests, therefore increasing the predictive value of the detection. The combination of the RILA assay and a method according to the invention could lead to a sensitivity of 0.90 and a specificity of 0.80 with a prevalence rate of 10%. This result could allow said test to be implemented in daily clinical practice.

A method according to the invention represents a useful tool within a therapeutic protocol, a precious help in decisions and may also be used within the prevention of radiotherapy induced toxicity.

A method according to the invention allows, from a simple blood collection and within five days, to determine the protein profile of individual radiosensitivity of tissues.

Rapidity, reproducibility and logistic simplicity of this test are strong arguments in favor of its implementation in clinical routine.

DETAILED DESCRIPTION OF THE INVENTION

The present invention will become more fully understood from the detailed description given herein and from the accompanying drawings, which are given by way of illustration only and do not limit the intended scope of the invention.

The present invention first relates to a method for the in vitro determination of the radiosensitivity of a subject, comprising the steps of:
- a) inducing an exogenous stress on a first fraction of a biological sample comprising cells,
- b) determining in the fraction of step a) the presence or the level of at least one compound,
- c) determining the presence or level of said at least one compound in a second fraction of said biological sample which has not been submitted to said exogenous stress,
- d) comparing the results of the determination of the presence or the level of said at least one compound in said first fraction and in said second fraction, and selecting at least one compound which is differentially expressed between said first and said second fraction,
- e) inducing an exogenous stress on a biological test sample comprising cells from said subject,
- f) determining in the test sample of step e) the presence or level of said at least one compound selected in step d)
- g) comparing the results of the determination of the presence or level of said at least one compound the results of step f) with the presence or level of the same compound in a biological reference sample, and
- h) determining from the comparison of step g) the radiosensitivity of said subject.

The term "radiosensitivity" relates to the intrinsic susceptibility of cells, tissues, organs and/or organisms to the harmful ionizing radiation damages, being either lethal or sub-lethal. In a method according to the present invention, said exposure to ionizing radiation takes place during a therapeutic radio-ionization, also called "radiotherapy" or "radiation therapy". Patients are submitted to a medical use of ionizing radiations to control or kill target cells according to clinical practice, and in particular to irradiating doses, extensively described and well known to physicians and radio-therapists.

The present invention first relates to a method for the determination and/or for the prediction of intrinsic radiosensitivity of a subject.

The mechanisms underlying the effects of irradiation in tissues involve molecular damage, targeting in particular DNA and plasma membrane, leading to the formation of free radicals and double-strand DNA breaks, and a multitude of cellular mechanisms, such as cell defense, apoptosis, stress response and repair processes (Lacombe et al., 2013).

In a method according to the invention, an "exogenous stress" is a stress induced on cells, tissues and/or organ by ionizing radiations or by a radiomimetic agent. In a method according to the invention, a "biological sample comprising cells" is isolated from the human body, and said exogenous stress is induced ex vivo to said biological sample comprising cells.

In a particular aspect of a method according to the invention, a "biological sample comprising cells" comprises any type of cells, wherein said cells are preferably chosen in the group consisting of: blood cells, more preferably white blood cells, even more preferably lymphocytes, and even more preferably CD4+ T lymphocytes or CD8+ T lymphocytes.

In a particular aspect of a method according to the invention, in steps a), b), c) and d), a biological sample comprising cells is isolated from a subject, or from a group of subjects, which are different from the subject for which it is desired to determine the radiosensitivity. According to this particular aspect of a method according to the invention, said biological sample comprising cells is isolated from the body of a human being. In a particular aspect of a method according to the invention, in steps a), b), c) and d), a biological sample comprising cells is isolated from a group of subjects suffering from the same illness than the subject for which it is desired to determine the radiosensitivity.

In a method according to the invention, a compound according to any one of steps b), c), d), f) and g) is preferably an intracellular compound. In a particular embodiment of the invention, said compound is a protein, with said protein being defined by its amino acids sequence. In a more particular embodiment, the invention comprises the detection of the presence or level of said protein or of a specific fragment thereof. By "specific fragment thereof" it is intended a fragment resulting for example from intracellular cleavage of a precursor, a protein being a fragment of a pre-pro-protein and of a pre-protein. In a particular embodiment, a "specific fragment" is a fragment or an epitope of the protein specifically recognized by a ligand of the protein, such as an antibody. In another particular embodiment, the invention comprises the detection of the presence or the level of a nucleic acid molecule encoding for said protein, said molecule being preferably a mRNA or a cDNA molecule, and being defined by its nucleotide sequence.

The determination of the "presence" of a compound leads to an indication of its presence or absence in a sample. The determination of the "level" of a compound may lead to an estimation of its quantity in a sample. The level of a compound in a sample may be expressed relatively to a reference sample, for example as a ratio or a percentage. Said level may also be expressed as the intensity or localization of a signal, according to the method used for said determination. Said level may also be expressed as a concentration of said compound in a sample. Preferentially, the concentration of said compound in a sample is expressed after normalization of the total concentration of relevant compounds in said sample. In a method according to the invention, the level of a compound in a first fraction of said biological sample is compared to the level of the same compound in a second fraction of said biological sample, wherein said comparison being possibly expressed as an estimation of the ratio of said compound in first and second fraction, or as a percentage of the level of said compound in one of the fractions. In a preferable embodiment, the quantitative levels of said compound in each fraction are statistically compared, according to methods known by a person skilled in the art, to demonstrate a differential expression of a compound within said two fractions.

In a method according to the invention, the level of said compound is determined (in step f)) in a test sample from said subject. In a particular embodiment, said test sample is a biological sample of the same nature than the biological sample used for selecting differentially expressed compounds (in step d)). As an example, samples of steps d) and f) may be collected and prepared according to the same method. In another particular embodiment, said test sample of step f) and said sample of step d) are biological samples which are prepared according to different methods.

In an embodiment of a method according to the invention, a reference sample is a sample prepared from the same subject before the induction of any exogenous stress, and is preferably a fraction of said biological test sample from said subject which has not been submitted to an exogenous stress. In another embodiment, a reference sample is a sample from a different subject for which the radiosensitivity is determined, for example by clinical detection.

In a particular embodiment, the present invention relates to a method for the in vitro determination of the radiosensitivity of a subject, comprising the steps of:
  a) inducing an exogenous stress on a biological test sample comprising cells from said subject,
  b) determining in the sample of step a) the presence or level of at least one compound, said compound being a protein chosen in the group consisting of: mitochondrial isocitrate dehydrogenase 2 (IDH2), DNA-(apurinic or apyrimidinic site) lyase (APEX1), Heat shock cognate protein 71 kDa (HSC70), adenylate kinase (AK2), annexin 1 (ANX1), a specific fragment thereof, a nucleic acid encoding the same and a combination thereof,
  c) comparing the presence or the level of said at least one compound with the presence or level of the same compound in a reference sample, and
  d) determining, from the comparison of step c), the radiosensitivity of said subject.

In an embodiment of a method according to the invention, the at least one compound differentially expressed in said biological sample, which were submitted or not, to an exogenous stress is chosen among proteins involved in mechanisms including metabolism, energy production, apoptosis, calcium binding protein, DNA damage repair and in the regulation of the level of intracellular Reactive Oxygen Species (ROS). In another particular embodiment, the at least one compound which is differentially expressed in samples submitted, or not, to an exogenous stress, is chosen among mitochondrial proteins. In a particular embodiment, proteins involved in the regulation of the level of intracellular Reactive Oxygen Species (ROS) are chosen in the group consisting of: mitochondrial isocitrate dehydrogenase 2 (IDH2), APEX, DNA-(apurinic or apyrimidinic site) lyase (APEX1) and Heat shock cognate protein 71 kDa (HSC70).

According to a particular embodiment, the invention comprises the determination in a biological test sample of the level of at least one of the proteins chosen in the group consisting of the proteins known to be involved in the cellular response to stress. In a more particular embodiment, a protein involved in the cellular response to stress is chosen in the group consisting of: mitochondrial isocitrate dehydrogenase 2 (IDH2), DNA-(apurinic or apyrimidinic site) lyase (APEX1) and Heat shock cognate protein 71 kDa (HSC70).

Mitochondrial isocitrate dehydrogenase 2 (NADP+) (amino acids sequence: SEQ ID No1, mRNA sequence: SEQ ID No6, GeneID: 3418; UniProt ID: P48735) is also defined as IDH2, ICD-M, IDP, NADP+-specific ICDH, Oxalosuccinate decarboxylase or is designed by gene name IDH2. It contains an N-terminal mitochondrial signal peptide and localizes to the mitochondria. It plays a key role in TCA cycle regulation in multiple tissues catalyzing the reversible conversion of isocitrate to α-ketoglutarate and NADP+ to NADPH. So, IDH2 is a critical component of the mitochondrial antioxidant pathway because NADPH is necessary for the regeneration of reduced glutathione (GSH), the major antioxidant responsible for preventing ROS damage (Lee et al., 2004). IDH2 is regulated by SIRT3 which is able to deacetylate and thus activate IDH2, leading to increased NADPH levels and an increased ratio of reduced-to-oxidized gluthatione in mitochondria (Someya et al., 2010). IDH2 may also play an important role in regulating the apoptosis induced by ionizing radiation (Lee et al., 2007).

APEX1 (amino acids sequence: SEQ ID No2, mRNA sequence: SEQ ID No7, GeneID: 328; UniProt ID: P27695) is named APEX nuclease (APEN), Apurinic-apyrimidinic endonuclease 1 (AP endonuclease 1, APE-1), REF-1, Redox factor-1 or designed by gene names APEX1, APE, APE1, APEX, APX, HAP1 or REF1). It is the main apurinic/apyrimidic endonuclease in eukaryotic cells which plays a central role in the DNA base excision repair pathway of all DNA lesions (uracil, alkylated and oxidized, and abasic sites), including single-strand breaks, and has also co-transcriptional activity by modulating genes expression directly regulated by either ubiquitous (i.e., AP-1, Egr-1, NF-κB, p53 and HIF) and tissue specific (i.e., PEBP-2, Pax-5 and -8, and TTF-1) transcription factors. In addition, it controls the intracellular redox state by inhibiting the reactive oxygen species (ROS) production through its inhibitory effect on Rac1, the regulatory subunit of a membrane nonphagocytic NAD(P)H oxidase system (Tell et al., 2009). These activities are located into two functionally distinct domains: the N-terminus is principally devoted to the redox activity while the C-terminus exerts the enzymatic activity on the abasic sites of DNA. Several studies demonstrated that functional polymorphisms of APEX1 may serve as radiation-induced predictive biomarkers. Yin et al. showed that polymorphisms of APEX1 may predict risk of radiation pneumonitis in patients with non-small cell lung cancer treated with definitive radiation therapy (Yin et al., 2011). Chang-Claude et al. demonstrated that APE1 [148]Glu allele may be protective against the development of acute side effects after radiotherapy (Chang-Claude et al., 2005).

Heat shock cognate 71 kDa protein (amino acids sequence: SEQ ID No3, mRNA sequence: SEQ ID No8, GeneID: 3312; UniProt ID: P11142) is named Heat shock 70 kDa protein 8 or designed by gene names HSPA8, HSC70, HSP73 or HSPA10. It is a constitutively expressed molecular chaperone which belongs to the heat shock protein 70 (HSP70) family. HSC70 shares some of the structural and functional similarity with HSP70 but also has different properties compared with it and other heat shock family members. HSC70 performs its full functions by the cooperation of co-chaperones. It interacts with many other molecules as well and regulates various cellular functions (Liu et al., 2012). It is also involved in various diseases and may become a biomarker for diagnosis and potential therapeutic targets for design, discovery, and development of novel drugs to treat various diseases (Liu et al., 2012). Studies demonstrated HSC70 overexpression provides a protective effect against both endogenous and exogenous generated ROS (Chong et al., 1998). It promotes ubiquitination and degradation of Nox proteins and therefore reduces ROS production (Chen et al., 2012).

In another particular embodiment, the present invention relates to the detection of the level of at least one compound, with said compound being a protein chosen in the group consisting of: adenylate kinase (AK2) and annexin A1 (ANX1).

Adenylate kinase 2 (amino acids sequence: SEQ ID No4, mRNA sequence: SEQ ID No9, GeneID: 204; UniProt ID:

P54819) is named AK 2, ATP-AMP transphosphorylase 2 or designed by gene names AK2 or ADK2. It is localized in the mitochondrial intermembrane space that controls adenine nucleotide levels. AK2 is a member of an ancient family of proteins, present from bacteria to humans, that catalyze the reversible reaction ATP+AMP=2ADP. The function of AK is classically described to be the maintenance of a constant concentration and fixed ratio of adenine nucleotides and the monitoring of cellular energy state through nucleotide sensing and signaling that is essential for maintenance and cell growth. Recent studies indicate that AK2 is also required for unfolded protein response (UPR) (Burkat et al., 2011). Alterations in endoplasmic reticulum (ER) homeostasis cause accumulation of misfolded/unfolded proteins in the ER and to maintain ER homeostasis, cells have evolved the UPR. The UPR is an essential adaptive intracellular signaling pathway that responds to metabolic, oxidative stress, and inflammatory response pathways.

ANX1 (amino acids sequence: SEQ ID No5, mRNA sequence: SEQ ID No10, GeneID: 301; UniProt ID: PO4083) is named Annexin I, Annexin-1, Calpactin II, Calpactin-2, Chromobindin-9, Lipocortin I, Phospholipase A2 inhibitory protein, p35 or designed by gene names ANXA1, ANX1 or LPC1. It was first described in the late 1970s. This 37 kDa calcium and phospholipid binding protein is a strong inhibitor of glucocorticoid-induced eicosanoid synthesis and PLA2. Recent interest in the biological activity of this intriguing molecule has unraveled important functional attributes of Annexin 1 in a variety of inflammatory pathways, on cell proliferation machinery, in the regulation of cell death signaling, in phagocytic clearance of apoptosing cells, and most importantly in the process of carcinogenesis (Lim et al., 2007).

Table 1 summarizes the identified proteins and their references.

TABLE 1

| Protein | Name and description | Protein reference and sequence | Nucleic acid reference and sequence |
| --- | --- | --- | --- |
| IDH2 | Homo sapiens isocitrate dehydrogenase 2 (NADP+), mitochondrial | UniProt ID: P48735, SEQ ID No 1 | mRNA, NCBI: NM_002168.2 SEQ ID No 6 |
| APEX1 | Homo sapiens APEX nuclease (multifunctional DNA repair enzyme) | UniProt ID: P27695, SEQ ID No 2 | transcript variant 4, mRNA, NCBI: NM_001244249.1 SEQ ID No 7 |
| HSC70 | Homo sapiens heat shock 70 kDa protein 8 (gene: HSPA8), | UniProt ID: P11142, SEQ ID No 3 | transcript variant 1, mRNA, NCBI: NM_006597.4, SEQ ID No 8 |
| AK2 | Homo sapiens adenylate kinase 2, nuclear gene encoding mitochondrial protein, | Uniprot ID: 54819, SEQ ID No 4 | transcript variant 3, mRNA, NCBI: NM_001199199.1, SEQ ID No 9 |
| ANX1 | Homo sapiens annexin A1 | UniProt ID: P04083, SEQ ID No 5 | mRNA, NCBI: NM_000700.1, SEQ ID No 10 |

In the present Application, proteins are defined by a particular amino acid sequence and by a corresponding specific nucleic acid sequence, being preferably a mRNA or cDNA nucleic acid sequence. The present invention comprises the detection of said proteins or nucleic acids, including any natural variant of said protein having a sequence chosen in the group consisting of SEQ ID No1 to SEQ ID No5, or variants of nucleic acid molecules having a sequence chosen in the group consisting of: SEQ ID No6 to SEQ ID No10. The present invention also comprises the detection of specific fragments of nucleic acid molecules having a sequence corresponding to a fragment of a sequence chosen in the group consisting of: SEQ ID No6 to SEQ ID No10 wherein said nucleic acid fragment correspond to a coding fragment of said nucleic acid molecule, or wherein said nucleic acid fragment encode for a specific fragment of a protein having a sequence chosen in the group consisting of: SEQ ID No1 to SEQ ID No5.

A method according to the present invention comprises the detection of variants of proteins comprising or having an amino acid sequence having at least 80%, preferably, 90%, more preferably 95% and even more preferably 98% identity with a sequence chosen in the group consisting of SEQ ID No1 to SEQ ID No5. The present invention comprises the detection of variants of mRNA comprising or having a nucleotide sequence having at least 80%, preferably, 90%, more preferably 95% and even more preferably 98% identity with a sequence chosen in the group consisting of SEQ ID No6 to SEQ ID No10. As used herein the term "identity" herein means that two amino acid sequences, or nucleic acid sequences, are identical (i.e. at the amino acid by amino acid, or nucleic acid by nucleic acid basis) over the window of comparison The term "percentage of sequence identity" is calculated by comparing two optimally aligned sequences over the window of comparison, determining the number of positions at which the identical amino acid residues occurs in both sequences to yield the number of matched positions, dividing the number of matched positions by the total number of positions in the window of comparison (i.e. the window size) and multiplying the result by 100 to yield the percentage of sequence identity. The percentage of sequence identity of an amino acid sequence can also be calculated using BLAST software with the default or user defined parameter. As applied to polypeptides, the term substantial identity means that two peptide sequences, when optimally aligned, share at least about 80% sequence identity, preferably at least about 90% sequence identity, more preferably at least about 95% sequence identity or more (e.g., 99% sequence identity). As used herein, a "derivative" or "sequence derived from" refers to an amino acid sequence having at least 80% identity, more preferably at least 90% identity and even more preferably at least 95% identity or more, such as 99% identity.

According to a preferred embodiment, the invention comprises the determination in a biological sample of the presence or level of a compound chosen in the group consisting of: mitochondrial isocitrate dehydrogenase 2 (IDH2), a specific fragment thereof, a nucleic acid encoding the same and a combination thereof.

According another embodiment, the invention comprises the determination in a biological sample of the presence or level of a compound chosen in the group consisting of: DNA-(apurinic or apyrimidinic site) lyase (APEX1), a specific fragment thereof, a nucleic acid encoding the same and a combination thereof.

According to another embodiment, the invention comprises the determination in a biological sample of the presence or level of a compound chosen in the group consisting of: Heat shock cognate protein 71 kDa (HSC70), a specific fragment thereof, a nucleic acid encoding the same and a combination thereof.

According to another embodiment, the invention comprises the determination in a biological sample of the presence or level of a compound chosen in the group consisting of: adenylate kinase (AK2), a specific fragment thereof, a nucleic acid encoding the same and a combination thereof.

According to another embodiment, the invention comprises the determination in a biological sample of the presence or level of a compound chosen in the group consisting of: annexin A1 (ANX1), a specific fragment thereof, a nucleic acid encoding the same and a combination thereof.

According to another preferred embodiment, the invention comprises the determination in a biological sample of the presence or level of:
- at least one compound chosen in the group consisting of: mitochondrial isocitrate dehydrogenase 2 (IDH2), a specific fragment thereof, a nucleic acid encoding the same and a combination thereof, and
- at least one compound chosen in the group consisting of: DNA-(apurinic or apyrimidinic site) lyase (APEX1), Heat shock cognate protein 71 kDa (HSC70), adenylate kinase (AK2), annexin A1 (ANX1), a specific fragment thereof, a nucleic acid encoding the same and a combination thereof.

According to another preferred embodiment, the invention comprises the determination in a biological sample of the presence or level of:
- at least one compound chosen in the group consisting of: DNA-(apurinic or apyrimidinic site) lyase (APEX1), a specific fragment thereof, a nucleic acid encoding the same and a combination thereof, and
- at least one compound chosen in the group consisting of: mitochondrial isocitrate dehydrogenase 2 (IDH2), Heat shock cognate protein 71 kDa (HSC70), adenylate kinase (AK2), annexin A1 (ANX1), a specific fragment thereof, a nucleic acid encoding the same and a combination thereof.

According to another preferred embodiment, the invention comprises the determination in a biological sample of the presence or level of:
- at least one compound chosen in the group consisting of: Heat shock cognate protein 71 kDa (HSC70), a specific fragment thereof, a nucleic acid encoding the same and a combination thereof, and
- at least one compound chosen in the group consisting of: mitochondrial isocitrate dehydrogenase 2 (IDH2), DNA-(apurinic or apyrimidinic site) lyase (APEX1), adenylate kinase (AK2), annexin A1 (ANX1), a specific fragment thereof, a nucleic acid encoding the same and a combination thereof.

According to another preferred embodiment, the invention comprises the determination in a biological sample of the presence or level of:
- at least one compound chosen in the group consisting of: adenylate kinase (AK2), a specific fragment thereof, a nucleic acid encoding the same and a combination thereof, and
- at least one compound chosen in the group consisting of: mitochondrial isocitrate dehydrogenase 2 (IDH2), DNA-(apurinic or apyrimidinic site) lyase (APEX1) and Heat shock cognate protein 71 kDa (HSC70), annexin A1 (ANX1), a specific fragment thereof, a nucleic acid encoding the same and a combination thereof.

According to another preferred embodiment, the invention comprises the determination in a biological sample of
- at least one compound chosen in the group consisting of: annexin A1 (ANX1), a specific fragment thereof, a nucleic acid encoding the same and a combination thereof, and
- at least one compound chosen in the group consisting of: mitochondrial isocitrate dehydrogenase 2 (IDH2), DNA-(apurinic or apyrimidinic site) lyase (APEX1), Heat shock cognate protein 71 kDa (HSC70), adenylate kinase (AK2), a specific fragment thereof, a nucleic acid encoding the same and a combination thereof.

According to a particular embodiment, a method according to the invention comprises the determination in a biological sample of the presence or level of at least two compounds, with said compounds being proteins chosen in the group consisting of: mitochondrial isocitrate dehydrogenase 2 (IDH2), adenylate kinase (AK2), annexin A1 (ANX1), DNA-(apurinic or apyrimidinic site) lyase (APEX1), Heat shock cognate protein 71 kDa (HSC70) a specific fragment thereof, a nucleic acid encoding the same and a combination thereof.

According to a particular embodiment, a method according to the invention comprises the determination in a biological sample of the presence or level of at least three compounds, with said compounds being proteins chosen in the group consisting of: mitochondrial isocitrate dehydrogenase 2 (IDH2), adenylate kinase (AK2), annexin A1 (ANX1), DNA-(apurinic or apyrimidinic site) lyase (APEX1), Heat shock cognate protein 71 kDa (HSC70), a specific fragment thereof, a nucleic acid encoding the same and a combination thereof.

According to a particular embodiment, a method according to the invention comprises the determination in a biological sample of the presence or the level of at least four compounds, with said compounds being proteins chosen in the group consisting of: mitochondrial isocitrate dehydrogenase 2 (IDH2), adenylate kinase (AK2), annexin A1 (ANX1), DNA-(apurinic or apyrimidinic site) lyase (APEX1), Heat shock cognate protein 71 kDa (HSC70), a specific fragment thereof, a nucleic acid encoding the same and a combination thereof.

According to a particular embodiment, a method according to the invention comprises the determination in a biological sample of the presence or the level of five compounds, with said compounds being proteins of the group consisting of: mitochondrial isocitrate dehydrogenase 2 (IDH2), adenylate kinase (AK2), annexin A1 (ANX1), DNA-(apurinic or apyrimidinic site) lyase (APEX1), Heat shock cognate protein 71 kDa (HSC70) a specific fragment thereof, a nucleic acid encoding the same and a combination thereof.

In another embodiment, the present invention relates to a method for the determination of the radiosensitivity of a subject, comprising the steps of:
a) inducing an exogenous stress on a biological test sample comprising lymphocytes from said subject,
b) determining the level of induced apoptosis in said biological test sample,
c) inducing an exogenous stress on a biological test sample from the same subject and determining the presence or the level of at least one compound, wherein said compound is chosen in the group consisting of: mitochondrial isocitrate dehydrogenase 2 (IDH2), DNA-(apurinic or apyrimidinic site) lyase (APEX1), Heat shock cognate protein 71 kDa (HSC70), adenylate kinase (AK2), annexin 1 (ANX1), a specific fragment thereof, a nucleic acid encoding the same and a combination thereof, d) comparing the presence or level of said at least one compound with the presence or level of the same compound in a reference sample, and e) determining, from the level of induced apoptosis of step b) and from the comparison of step d), the radiosensitivity of said subject.

According to this particular embodiment, a method according to the invention comprises the detection of lymphocytes apoptosis induced by an exogenous stress and the determination of the radiosensitivity of a subject according to a method of the invention. In a more particular embodiment of the invention, lymphocytes apoptosis is induced ionizing radiations. In an even more particular embodiment, the detection of radiation-induced lymphocytes apoptosis is performed by a RILA assay such as described in Ozsahin et al. (2005). In another particular embodiment, apoptosis is detected by a method chosen in detection of ADN fragmentation (Comet assay, TUNEL assay) and detection of mitochondrial pathway (Detection of caspase 3, detection of cytochrome C).

In a particular embodiment, the detection of lymphocytes apoptosis and the determination of the radiosensitivity of a subject according to a method of the invention are performed on different biological samples from the same subject. In another particular embodiment, the detection of lymphocytes apoptosis and the determination of the radiosensitivity of a subject according to a method of the invention are performed on biological samples of the same nature, for example a white cells extract from blood. In an even more particular embodiment, the method according to the invention and a RILA-assay are performed on different fractions of the same biological sample comprising lymphocytes from the subject.

In another particular embodiment, the present invention relates to a method for predicting the susceptibility of late radio-induced toxicity in a subject, comprising:
a method for the in vitro determination of the radiosensitivity of a subject according to the invention, and
a step of predicting the susceptibility to late radio-induced toxicity of said subject if said at least one compound is present in said biological test sample and absent in said reference sample and/or if the level of said at least one compound in said biological test sample is superior to the level of the same compound in said reference sample.

The present invention relates to a method for determining the radiosensitivity, or radiosensibility, of tissues and/or cells of a subject, wherein tissues and/or cells submitted to ionizing radiation comprise tissues and/or cells specifically targeted by the irradiation, and also normal or "healthy" tissues and/or cells which are not specifically targeted by the radiotherapy but are included in the irradiated volume of tissues and/or cells. In a particular embodiment, the present invention relates to a method for determining the radiosensitivity, or radiosensibility, of healthy tissues of the patient, wherein "healthy tissues (or cells)" are defined as tissues (or cells) not specifically targeted by the radiotherapy. Said "healthy tissues" relate to tissues or cells adjacent or surrounding the target tissue. "Late side-effects" or "long term side effects" or "late toxicity" can appear beginning 3 to 6 months after irradiation. The symptoms are multiple, often including fibrosis, tissue necrosis, atrophy, vascular damage and in very severe cases, radiation-induced cancers and show worsening over time, even 20-34 years after radiotherapy (Lacombe et al., 2013). In a particular aspect, late toxicity is radiation induced lung inflammation.

In a particular embodiment, a method according to the invention allows the detection of patients susceptible to be affected by late radio-hypersensitivity. The severity of late toxicity symptoms are classified according to grades. In a particular aspect, a method according to the invention allows the determination of late radiosensitivity of grade 2 and higher (grade 3 and more).

According to a particular embodiment, the present invention relates to a method for the in vitro determination of the radiosensitivity of a subject, said method comprising:
the determination of the presence or level of at least one compound chosen in the group consisting of: IDH2, APEX1, HSC70, AK2 and ANX1, a specific fragment thereof, a nucleic acid encoding the same and a combination thereof,
at least another predictive method of radiosensitivity such as described in the prior art. Said other predictive method is possibly, but is not limited to, a RILA assay or a SNP detection assay.

According to a particular embodiment, the present invention relates to a method for the in vitro determination of the radiosensitivity of a subject, comprising:
the determination of the presence or level of IDH2, a specific fragment thereof, a nucleic acid encoding the same and a combination thereof,
at least another predictive method of radiosensitivity, preferably a RILA assay or a SNP detection assay (Azria et al., 2008).

According to another particular embodiment, the present invention relates to a method for the in vitro determination of the radiosensitivity of a subject, comprising:
the determination of the presence or level of IDH2, a specific fragment thereof, a nucleic acid encoding the same and a combination thereof,
the determination of the presence or level of at least one compound chosen in the group consisting of: APEX1, HSC70, AK2 and ANX1, a specific fragment thereof, a nucleic acid encoding the same and a combination thereof,
at least another predictive method of radiosensitivity, preferably a RILA assay or a SNP detection assay.

According to another particular embodiment, the present invention relates to a method for the in vitro determination of the radiosensitivity of a subject, comprising:
the determination of the presence or level of: 1) IDH2, a specific fragment thereof or a nucleic acid encoding the same, 2) APEX1, a specific fragment thereof or a nucleic acid encoding the same, 3) HSC70, a specific fragment thereof or a nucleic acid encoding the same, 4) AK2, a specific fragment thereof or a nucleic acid encoding the same, 5) ANX1, a specific fragment thereof or a nucleic acid encoding the same, and
at least another predictive method of radiosensitivity, preferably a RILA assay or a SNP detection assay.

In a particular embodiment, a method for the determination of the radiosensitivity according to the invention is performed on a biological sample of a subject for which the results of an induced lymphocyte apoptosis tests are known. In a more particular embodiment, a method for the determination of the radiosensitivity according to the invention is performed on a biological sample of a subject for which the results of RILA assay are indicative of a low level of induced apoptosis, and preferably an induced apoptosis inferior to 16%.

In a particular embodiment, the present invention relates to a method wherein said exogenous stress is induced by at least a method chosen among the following: irradiation and contact with at least one radiomimetic agent. In a first particular embodiment, said exogenous stress is generated by irradiation. In another particular embodiment, said exogenous stress is generated by contact with at least one radiomimetic agent. In another particular embodiment, said exogenous stress is generated by a irradiation and by contact with at least one radiomimetic agent.

In a more particular embodiment, said exogenous stress is induced by a irradiation, wherein the irradiation dose is comprised between about 0.1 and about 16 Gy, preferably between about 2 and about 14 Gy, more preferably superior to about 4 Gy, preferably between about 4 and about 12 Gy, preferably between about 6 and about 10 Gy, and more preferably of about 8 Gy. The term "about" means a possible variation of +/−10% in the administered dose. In a method according to the invention, biological samples are irradiated by 8 Gy X-Rays.

In a particular embodiment, samples receive 8 Gy with a dose debit of 1 Gy/min. Parameters used for irradiation are indicative and may be adapted by persons skilled in the art according to their practice and to the device used for linear acceleration. In a particular embodiment, irradiation is performed through a 15 mm thick polystyrene 6-wells cell culture plate. Samples are irradiated by a 6 MV beam, with a source to surface distance of 145 cm and an irradiation field of 25×25 cm at the collimator. As an example, for delivering a 8 Gy dose, when using a "GE Saturne 43" linear accelerator, a dose of 1520 MU (Monitor Units) has to be delivered by the accelerator, whereas when using a "Varian" linear accelerator, a dose of 1600 MU has to be delivered by the accelerator.

In another particular embodiment, said exogenous stress is induced by contacting the sample with at least one radiomimetic agent. A "radiomimetic agent" is a substance inducing effects on cells which are similar to those provoked by ionizing radiations, a radiomimetic agent may be considered as "mimicking" at least a part of the effects of ionizing radiations on cells. As non-limiting examples, a radiomimetic agent may provoke single strand and/or double strand DNA breaks or may lead to the presence of free radicals in the cell. In a particular embodiment, the sample is contacted with a single radiomimetic agent. In another particular embodiment, the sample is contacted with two or more radiomimetic agents, said agents being used simultaneously or successively. A radiomimetic agent usable for a method according to the invention may be chosen in the group consisting of: aphidicolin, bleomycin, enediyne antibiotics and hydrogen peroxyde. Bleomycine is known to provoke single or double strand DNA breaks, whereas hydrogen peroxide is known to induce free radicals. A method according to the invention is not limited to the use of a particular radiomimetic agent and a person skilled in the art will easily choose the adapted agent for practicing a particular method according to the invention. According to said particular embodiment, said contact with a radiomimetic agent is performed following conditions such as described in Kennedy et al. (2006), Adema et al. (2003), Cloos J et al. (1999) or Tedeschi et al. (2004). In a particular embodiment, lymphocytes apoptosis in a method according to the invention is induced by contact with a radiomimetic agent such as described in the present application.

In another particular embodiment, a method according to the invention comprises the preparation of a biological sample, said sample being chosen in the group consisting of: whole blood, whole blood extract containing cells, whole blood extract containing white cells, whole blood extract containing lymphocytes and whole blood extract containing CD4+ and/or CD8+ T lymphocytes.

Whole blood extracts containing cells are prepared according to methods well known by persons skilled in the art of manipulating blood samples for biological tests. Such method may include, for example, separation of blood constituents on Ficoll gradients, rapid blood cell separation method using RosetteSep™ from StemCell or using flow cytometer.

A method according to the present invention comprises the preparation of biological samples and the induction of an exogenous stress on a fraction of said sample.

In a more particular embodiment, the present invention relates to a method wherein biological samples are prepared according to the following method:
  a) isolating lymphocytes from said whole blood extract,
  b) irradiating said isolated lymphocytes of step a), and
  c) extracting proteins from the lymphocytes of step b).

In a more particular embodiment, the present invention relates to a method wherein the presence or level of at least one compound is determined by at least one method chosen in the group consisting of: a method based on immunodetection, a method based on western blot, a method based on chromatography, and preferably liquid chromatography, a method based on mass spectrometry, a method based on flow cytometry and a method for specific nucleic acid detection.

These methods are well known by a person skilled in the art of detecting and quantifying compounds, and particularly proteins, wherein the presence and level of expression of proteins can be determined directly or be analyzed at the nucleic acid level by detecting, and preferably quantifying, protein-specific nucleic acids, and particularly mRNA.

In a first step, proteins and/or nucleic acids are isolated from the biological sample. A method according to the invention may include protein extraction, purification and characterization, using well known biochemistry methods.

Methods for the specific detection of a protein based on mass spectrometry include, but are not limited to, Selected Reaction Monitoring (SRM) and Multiple Reaction Monitoring (MRM). Methods based on flow cytometry include, but are not limited to, a multiplex assay such as Luminex®XMAP, combining flow cytometry with microspheres and lasers.

Methods for the specific detection of nucleic acids involve methods for analyzing DNA and RNA, particularly mRNA. The methods classically used in molecular biology are well known to those skilled in the art of analyzing nucleic acids and are fully described in the literature (Maniatis T. et al., Edition 1999). Nucleic acid molecules comprising nucleic acid sequences having at least 80% of identity with a sequence chosen in the group consisting of SEQ ID No6 to SEQ ID No10 are preferably sequences coding for the same sequences of amino acids, in relation with the degeneration of the genetic code, or complementary sequences which are capable of specifically hybridizing with a sequence chosen in the group consisting of SEQ ID No6 to SEQ ID No10 under strong stringency conditions. Strong stringency conditions means that conditions of temperature and ionic force are selected to allow the maintained hybridization between two complementary nucleic acid molecules or fragments. In an embodiment, a method according to the invention comprises the use of short oligonucleotidic sequences able to specifically hybridize to mRNA molecules of SEQ ID No6 to SEQ ID No10.

In a particular embodiment, a method according to the invention comprises the extraction of RNA from the biological sample. After extraction with Trizol reagent, transcriptional responses genome wide is performed by global run on sequencing. A transcriptomic analysis through RNA sequencing (RNAseq) allows the quantification of transcripts. RNAseq allows detection of alternative spliced transcripts as well as SNPs. Furthermore, in addition to transcriptionally modulated coding genes, non coding genes such as those producing long non-coding RNAs or micro-RNAs can be followed.

In a particular embodiment, the present invention relates to a method for the in vitro determination of the radiosensitivity of a subject or for predicting the susceptibility of late radio-induced toxicity in a subject, said method comprising the detection of the presence or level of at least two of the proteins chosen in the group consisting of: mitochondrial isocitrate dehydrogenase 2 (IDH2), DNA-(apurinic or apyrimidinic site) lyase (APEX1), Heat shock cognate protein 71 kDa (HSC70), adenylate kinase (AK2), and annexin 1 (ANX1).

In another particular embodiment, the present invention relates to a method for the in vitro determination of the radiosensitivity of a subject or for predicting the susceptibility of late radio-induced toxicity in a subject, said method comprising the detection of the presence or level of mitochondrial isocitrate dehydrogenase 2 (IDH2) and DNA-(apurinic or apyrimidinic site) lyase (APEX1). In another particular embodiment, the present invention relates to a method for the in vitro determination of the radiosensitivity of a subject or for predicting the susceptibility of late radio-induced toxicity in a subject, said method comprising the detection of the presence or level of mitochondrial isocitrate dehydrogenase 2 (IDH2) and of Heat shock cognate protein 71 kDa (HSC70). In another particular embodiment, the present invention relates to a method for the in vitro determination of the radiosensitivity of a subject or for predicting the susceptibility of late radio-induced toxicity in a subject, said method comprising the detection of the presence or level of mitochondrial isocitrate dehydrogenase 2 (IDH2) and of adenylate kinase (AK2). In another particular embodiment, the present invention relates to a method for the in vitro determination of the radiosensitivity of a subject or for predicting the susceptibility of late radio-induced toxicity in a subject, said method comprising the detection of the presence or level of mitochondrial isocitrate dehydrogenase 2 (IDH2) and of annexin 1 (ANX1).

In another particular embodiment, the present invention relates to a method for the in vitro determination of the radiosensitivity of a subject or for predicting the susceptibility of late radio-induced toxicity in a subject, said method comprising the detection of the presence or level of at least three of the proteins chosen in the group consisting of: mitochondrial isocitrate dehydrogenase 2 (IDH2), DNA-(apurinic or apyrimidinic site) lyase (APEX1), Heat shock cognate protein 71 kDa (HSC70), adenylate kinase (AK2), and annexin 1 (ANX1).

In another particular embodiment, the present invention relates to a method for the in vitro determination of the radiosensitivity of a subject or for predicting the susceptibility of late radio-induced toxicity in a subject, said method comprising the detection of the presence or level of the five proteins from the group consisting of: mitochondrial isocitrate dehydrogenase 2 (IDH2), DNA-(apurinic or apyrimidinic site) lyase (APEX1), Heat shock cognate protein 71 kDa (HSC70), adenylate kinase (AK2), and annexin 1 (ANX1).

According to the present invention, the method allows the detection of the radiosensitivity of a subject which is affected by a disease susceptible to be treated by radiotherapy. In a particular embodiment, said disease is selected in the non-limiting group consisting of: cancer, disease of Basedow (or Grave's disease), hyperthyroidism, pituitary adenome (or adenoma), meningiome (or meningioma) and talalgy (or talalgia).

In a particular embodiment, a method according to the invention allows to determine radiosensitivity of subject affected by cancer, including, but not limited to, breast cancer, colo-rectal cancer, prostate cancer, lung cancer, head and neck cancer.

According to a particular aspect, the present invention relates to the use of at least one compound chosen in the group consisting of: mitochondrial isocitrate dehydrogenase 2 (IDH2), DNA-(apurinic or apyrimidinic site) lyase (APEX1), Heat shock cognate protein 71 kDa (HSC70), adenylate kinase (AK2), and annexin 1 (ANX1) or a combination thereof, as markers for the in vitro determination of the radiosensitivity of a subject or for predicting the susceptibility of late radio-induced toxicity.

According to another embodiment, the present invention relates to the use of mitochondrial isocitrate dehydrogenase 2 (IDH2) and of at least one compound chosen in the group consisting of: APEX1, HSC70, AK2 and ANX1 or a combination thereof, as markers for the in vitro determination of the radiosensitivity of a subject or for predicting the susceptibility of late radio-induced toxicity of a subject.

In a more particular embodiment, the present invention relates to the use of at least two compounds chosen in the group consisting of: IDH2, APEX1, HSC70, AK2 and ANX1 or a combination thereof, as markers for the in vitro determination of the radiosensitivity of a subject or for predicting the susceptibility of late radio-induced toxicity. In an even more particular embodiment, the present invention relates to the use of at least three compounds chosen in the group consisting of: IDH2, APEX1, HSC70, AK2 and ANX1 or a combination thereof, as markers for the in vitro determination of the radiosensitivity of a subject, or for predicting the susceptibility of late radio-induced toxicity in a subject. In another particular embodiment, the present invention relates to the use of at least four compounds chosen in the group consisting of: IDH2, APEX1, HSC70, AK2 and ANX1 as markers for the in vitro determination of the radiosensitivity of a subject, or for predicting the susceptibility of late radio-induced toxicity in a subject. In an even more particular embodiment, the present invention relates to the use of a combination of IDH2, APEX1, HSC70, AK2 and ANX1 as markers for the in vitro determination of the radiosensitivity of a subject, or for predicting the susceptibility of late radio-induced toxicity in a subject.

According to another embodiment, the present invention relates to the use of a at least one compound chosen in the group consisting of: IDH2, APEX1, HSC70, AK2 and ANX1, or a combination thereof, as markers for the in vitro determination of the radiosensitivity of a subject, or for predicting the susceptibility of late radio-induced toxicity in a subject, in a method according to the invention.

According to another particular embodiment, the present invention relates to a kit usable for the in vitro determination of the radiosensitivity of a subject or for predicting the susceptibility of late radio-induced toxicity in a subject, said kit comprising at least a reagent for the specific detection of at least one compound chosen in the group consisting of: mitochondrial isocitrate dehydrogenase 2 (IDH2), DNA-(apurinic or apyrimidinic site) lyase (APEX1), Heat shock cognate protein 71 kDa (HSC70), adenylate kinase (AK2), and annexin 1 (ANX1), and a reagent for the induction and/or the detection of cell apoptosis. An agent for the detection of cell apoptosis may be any agent used in such a method by a person skilled in the art. Examples of methods and agents usable for the detection of cell apoptosis are detection of ADN fragmentation (Comet assay, TUNEL assay), detection of mitochondrial pathway (Detection of caspase 3, detection of cytochrome C), Annexin A5.

In said particular embodiment, a reagent for the specific detection of at least one of the compounds chosen in the group consisting of: IDH2, APEX1, HSC70, AK2 and ANX1 in a kit according to the invention is an antibody or a ligand specific for one of said proteins, including its natural variants, or of a specific fragment thereof. In another particular embodiment, a reagent for the specific detection of at least one of the compounds chosen in the group consisting of: IDH2, APEX1, HSC70, AK2 and ANX1 in a kit according to the invention is a nucleic acid molecule able to bind specifically to a nucleic acid molecule encoding for a protein chosen in the group consisting of: IDH2, APEX1, HSC70, AK2 and ANX1, or for a fragment thereof.

In a more specific embodiment, a reagent for the specific detection of at least IDH2, APEX1, HSC70, AK2 and ANX1 in a kit according to the invention is a nucleic acid which hybridizes in stringent condition with a nucleic acid molecule comprising a sequence chosen in the group consisting of SEQ ID No6 to SEQ ID No10, or a fragment thereof which encodes for a specific fragment of IDH2, APEX1, HSC70, AK2 or ANX1.

In a more specific embodiment, the present invention relates to a kit comprising at least a reagent for the specific detection of IDH2 and reagents for the specific detection of at least APEX1, HSC70, AK2 and ANX1, or a specific fragment thereof.

In a more particular embodiment, the present invention relates to a kit comprising at least reagents for the specific detection of at least two of the compounds chosen in the group consisting of IDH2, APEX1, HSC70, AK2 and ANX1, or a specific fragment thereof.

In a more particular embodiment, the present invention relates to a kit comprising at least reagents for the specific detection, respectively, of at least three of the compounds chosen in the group consisting of: IDH2, APEX1, HSC70, AK2 and ANX1, or a specific fragment thereof.

In a more particular embodiment, the present invention relates to a kit comprising at least reagents for the specific detection, respectively, of at least four of the compounds chosen in the group consisting of: IDH2, APEX1, HSC70, AK2 and ANX1, or a specific fragment thereof.

In an even more particular embodiment, the present invention relates to a kit comprising at least reagents for the specific detection, respectively, of the following compounds: IDH2, APEX1, HSC70, AK2 and ANX1, or a specific fragment thereof.

The following examples are provided herein for purposes of illustration only and are not intended to be limiting unless otherwise specified.

BRIEF DESCRIPTION OF THE DRAWINGS

FIG. 5A: Western blot analysis of the expression of CTGF, a-sm actin, HSC70, APEX1 in tissues after contact, or not, with fibrose-inducing TGFb1.

FIG. 5B: Histogram representation of expression of CTGF, a-sm actin, HSC70, APEX1 in tissues after contact, or not, with fibrose-inducing TGFb1.

EXAMPLES

Example 1: Lymphocyte Apoptosis Assay

The inventors previously developed a rapid and reproducible assay called RILA (radiation-induced lymphocyte apoptosis) that measures apoptosis in CD4 and CD8 T-lymphocytes after irradiation (0.5-8 Gy) via flow cytometry. This measure is based on the decrease in nuclear DNA fluorescence due to specific chromatin changes that accompany apoptosis. RILA was used as a main stratification factor in a phase II randomized study in early breast cancer following conservative surgery comparing postoperative radiotherapy either concomitantly or sequentially with letrozole in 150 patients, the primary end-point being breast fibrosis (Azria et al., 2010). No patient with a RILA>16% was found to exhibit radiation-induced late effects, indicating the high negative predictive value of this test. All patients with grade 2 or worse subcutaneous fibrosis had a RILA<16%, confirming the predictive value of the test. However, among patients with a RILA<16%, 20% suffered from late radio-toxicity and 80% did not, indicating a weak positive predictive value for RILA. Sensitivity of RILA assay is 0.70, whereas specificity of this test is inferior to 0.50. Four patients treated for a breast cancer, and with a low RILA value were selected from the prospective study mentioned above. Two patients developed a severe (higher than grade 2) fibrosis toxicity (patients No1 and No2), whereas patients had no toxicity at least four years after the end of radiotherapy treatment whereas (patients No3 and No4).

Example 2: Identification of Predictive Markers of Late Induced Cytotoxicity

Figure 1:
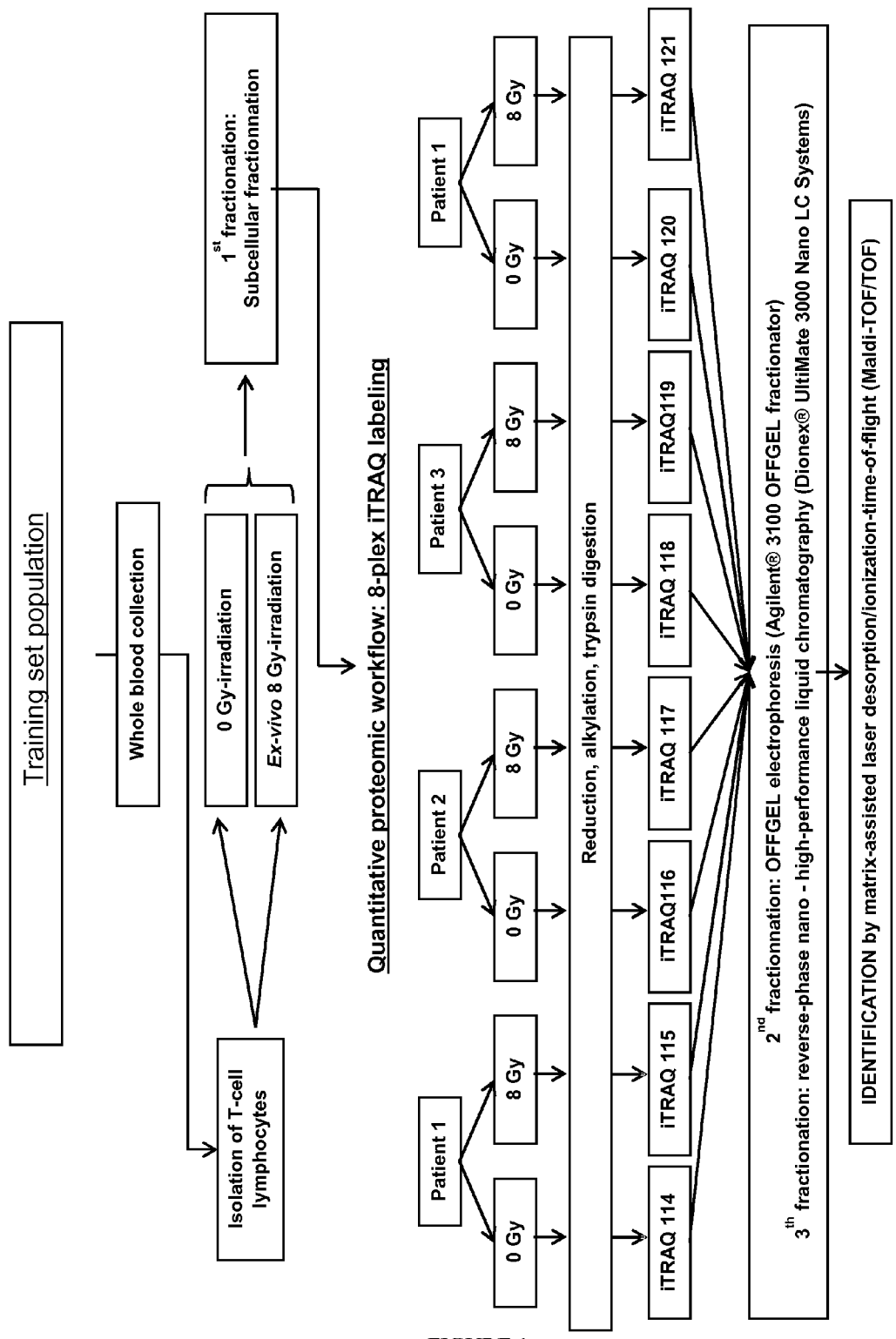
FIG. 1: Schematic representation of the protocol for identification of proteins associated with late radio-toxicity from a whole blood collection from four patients. Patient 1: toxicity superior to grade 2 at month 36 after radiotherapy (RT). Patient 2: toxicity superior to grade 2 at month 48 after RT. Patient 3: no toxicity at month 48 after RT. Patient 4: no toxicity at month 54 after RT.

The protocol for identifying predictive markers is schematized in FIG. 1. From the four patients previously mentioned, 40 ml of total blood was collected in heparinized tubes. T-lymphocytes were isolated from whole blood by negative selection using rosette (RosetteSep®, StemCell Technology) according to the manufacturer's instructions, followed by a Ficoll gradient (GE Healthcare). Lymphocytes were then cultivated in RPMI medium with 10% FCS for 24 h at 37° C. and 5% CO2. Half of the lymphocytes have then been irradiated in vitro at 8 Gy. Irradiated and non-irradiated lymphocytes were then cultivated again at 37° C. and 5% CO2 for 48 h. After this incubation time, lymphocytes from each patient were then submitted to subcellular fractioning (ProteoExtract® Subcellular Proteome Extraction Kit (Cat. No. 539790), Merckmillipore) allowing to isolate cytosolic, membranar and nuclear fractions. Each of these fractions was then analyzed by using a quantitative proteomics workflow using an 8-plex iTRAQ labeling. After several fractionations to optimize resolution of analysis (off gel fractionation followed by nanoliquid chromatography), proteins were identified by tandem mass spectrometry (4800 plus MALDI TOF/TOF).

Briefly, 50 µg of proteins from each patient, from irradiated and non-irradiated lymphocytes, were reduced, alkylated and trypsinized before being labelled with an iTRAQ tag. For each fraction (cytosolic, membrane and nuclear), the 8 labellings for each patient, including fractions with irradiated and non-irradiated lymphocytes, were pooled and fractioned by isoelectrofocalisation in a liquid medium type Offgel (Agilent 3100 Offgel fractionator). 12 subfractions are therefore obtained. Each of these subfractions is then separated by reverse phase high-performance liquid nanochromatography (HPLC) (Ultimate 3000 LC Systems, Dionex) coupled to a spotting automat. The 12 Offgel subfractions are then put, with 600 spots for each, on MALDI plates. HPLC was performed in duplicate. 8 MALDI plates have been used for each fraction (cytosolic, membrane and nuclear), leading to a total of 24 plates. Identification by mass spectrometry was then performed on a system MALDI TOF/TOF® 4800 Proteomics Analyzer d'AbSciex. m/z 700-1400 spectra were acquired in a positive mode, using 1500 laser impulsions. Precursor ions of the ten most abundant peptides, with a signal/noise ratio superior or equal to 50 are selected for a MS/MS analysis using 3500 laser impulsions of m/z 300-1500. MS/MS spectra are compared to Uniprot protein database (uniprot_sprot300108) from the European Institute for Bioinformatics, using the ProteinPilot® 2.0 software and the Paragon method (Ab Sciex, Software revision 50861). Proteins corresponding to a unique peptide with a high confidence interval (>95%) are considered as positively identified.

Results:

A comparison of ratios between proteins differentially expressed at 0 Gy and 8 Gy between the two patients having developed a late toxicity and the two patients without any toxic effect was performed. More than 1300 total proteins were identified with high confidence (95%, one unique peptide). At 0 Gy, 135 proteins were differentially expressed between patients with or without severe radio-induced toxicity (p<0.05). In irradiated T-lymphocytes (8 Gy), 107 proteins were differentially expressed between patients with or without severe radio-induced toxicity (p<0.05). The proteins chosen for the validation step are those differentially expressed at 8 Gy, with the highest protein expression ratio (>1.5) and that showed no difference expression ratio in 0 Gy controls.

Five proteins have been selected for consecutive validation: isocitrate dehydrogenase 2 (NADP+) (IDH2), DNA-(apurinic or apyrimidinic site) lyase (APEX1), Heat shock cognate 71 kDa (HSC70), adenylate kinase 2 (AK2) and annexin 1 (ANX1). These proteins are involved in several mechanisms including metabolism and energy production, apoptosis, calcium binding protein, and DNA damages repair.

Example 3: Confirmation of the Differential Expression of Biomarkers in a Larger Number of Patients after Radiotherapy These five proteins were validated by western blot analysis on an additional population of 18 patients, with 5 patients having developed a grade ≥2 breast fibrosis and 13 patients having developed only weak or no toxicity. All these 10 patients presented a low RILA value. Blood samples were collected and treated as described in the previous example, until the post-irradiation incubation. Lymphocytes were then lysed in a RIPA buffer. Proteins were then quantified then 10 µg of each were put on a polyacrylamide gel 12% for a Western Blot. After migration and transfer on a PVDF membrane for 1 h at 300 mA at 4° C., le membrane was then saturated for 2 hours in PBS-Tween 0.05%-milk 5% and the antibodies against the proteins of interest were incubated overnight at 4° C. under agitation in the same saturating buffer. After 5 successive 5 min washings in PBS-Tween 0.05% buffer, the secondary antibody was then added for 1 h at room temperature in a PBS-Tween 0.05% buffer. After 5 other 5 min washings in PBS-Tween 0.05% buffer, revealing was performed by ECL.

Figure 2:
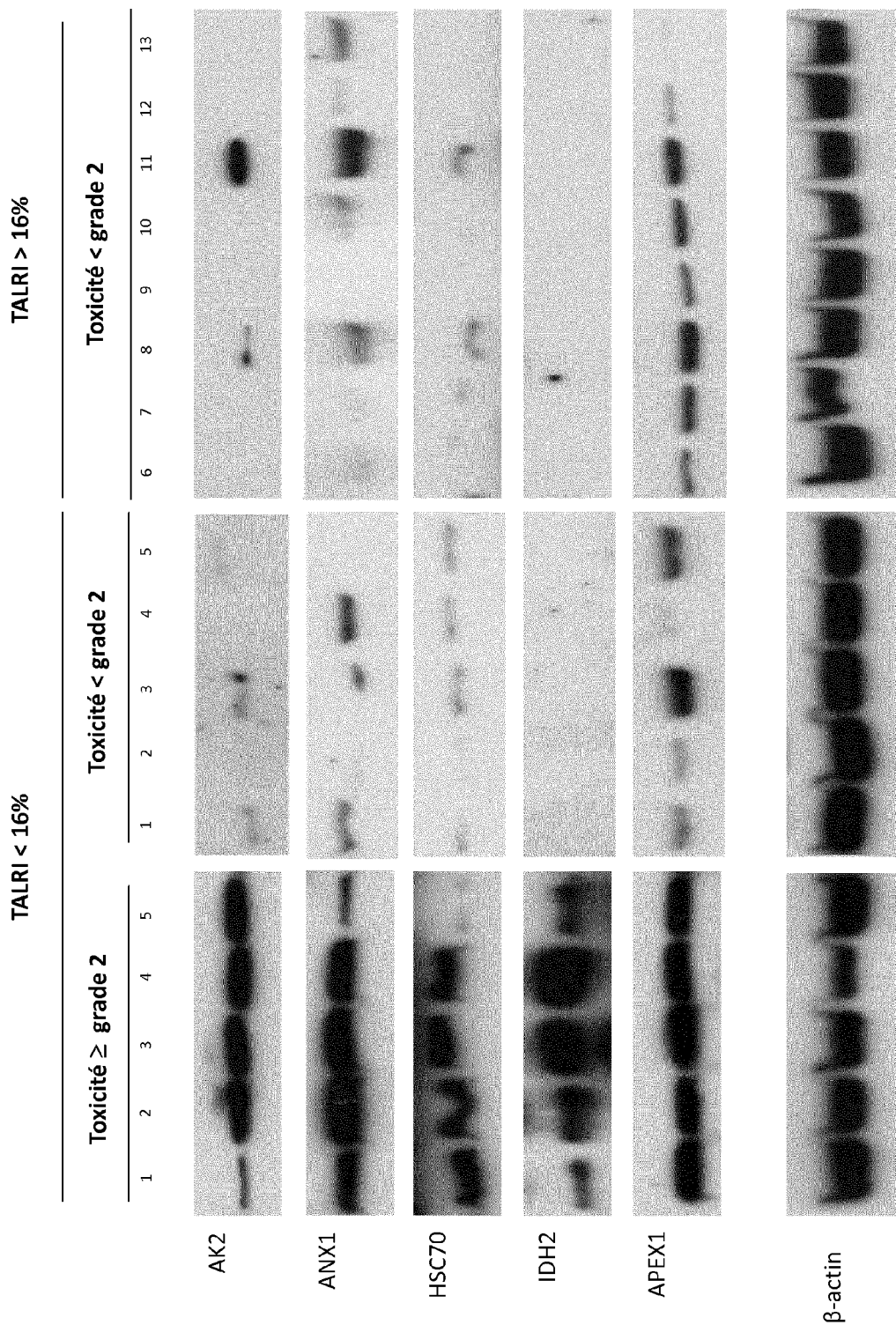
FIG. 2: Validation of the expression level of AK2, ANX1, HSC70, IDH2 and APEX1 depending of the observed late radiotoxicity. B-actin is a control of the amount of proteins. Left panel: Western blot analysis of protein extracts from patients for who the result of RILA assay (=TALRI on the figure) was inferior to 16% and toxicity superior to grade 2 toxicity. Central panel: Western blot analysis of protein extracts from patients for who the result of RILA assay was inferior to 16% and toxicity inferior to grade 2 toxicity. Right panel: Western blot analysis of protein extracts from patients for who the result of RILA assay was superior to 16% and toxicity inferior to grade 2 toxicity.
Figure 3:
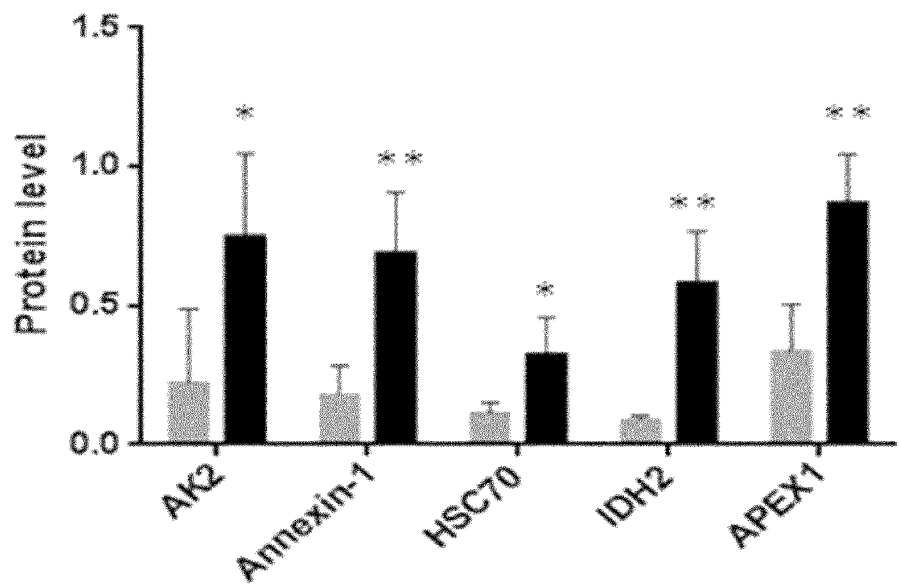
FIG. 3: Quantitative detection of AK2, ANX1, HSC70, IDH2 and APEX1. Histogram representation of the protein level in extracts from patients suffering from toxicity inferior to grade two (clear left panel) and from patients suffering from toxicity superior to grade two (dark right panel), for, respectively from left to right, AK2, ANX1, HSC70, IDH2 and APEX1.

Results:

Results show that all of these five proteins were overexpressed in irradiated T-lymphocytes from the patients having suffered from severe toxicity comparatively to patients with no late toxicity (FIG. 2). Quantitative expression analysis confirmed the statistical significance of these differences (Table 2 and FIG. 3).

TABLE 2

| | Median, [min-max] | | | | | | |
|---|---|---|---|---|---|---|---|
| | Tox < gr.2; RILA < 16% (n = 5)[1] | Tox < gr.2; RILA > 16% (n = 8)[2] | Tox < gr.2; (n = 13) [1] + [2] | Tox ≥ gr.2 (n = 5) [3] | P value [1] vs. [3] | [2] vs. [3] | [1] + [2] vs. [3] |
| AK2 | 0.22, [0.08-0.69] | 0.23, [0.07-0.85] | 0.23, [0.07-0.85] | 0.76, [0.26-1.06] | 0.016 | 0.030 | 0.007 |
| ANX1 | 0.18, [0.07-0.32] | 0.38, [0.09-0.83] | 0.30, [0.07-0.83] | 0.69, [0.34-0.93] | 0.002 | 0.037 | 0.004 |
| HSC70 | 0.12, [0.07-0.17] | 0.26, [0.08-0.74] | 0.20, [0.07-0.74] | 0.33, [0.10-0.42] | 0.045 | 0.127 | 0.046 |
| IDH2 | 0.09, [0.07-0.11] | 0.23, [0.08-0.69] | 0.18, [0.07-0.69] | 0.58, [0.34-0.80] | 0.004 | 0.009 | 0.002 |
| APEX1 | 0.34, [0.11-0.53] | 0.71, [0.14-1.88] | 0.56, [0.11-1.88] | 0.87, [0.72-1.12] | 0.001 | 0.489 | 0.059 |

As a conclusion, the five identified biomarker allow to discriminate among patients with were initially identified as susceptible of radio-sensibility, with a weak RILA. Therefore, the present test not only confirms the results of RILA but also demonstrates a more discriminant ability.

Example 4: Proteomic Analysis of Samples from Patients

Sample Collection:

21 ml heparinized whole blood is collected from each patient, preferably before starting radiotherapy.

T Lymphocytes Separation:

Immediately, T lymphocytes are purified by negative selection using the Rosette tetrameric complex system (RosetteSep, StemCell Technologies) following manufactory recommendations. This protocol allows the recovering of 7.5 to 15 million cells per patient.

T Lymphocyte Primary Cell Culture:

Purified T lymphocytes are cultured in two dishes containing RPMI 1640 medium (Gibco BRL Invitrogen) supplemented with 10% FCS during 24 h.

T Lymphocyte Cell Culture Irradiation:

For each patient, one cell culture dish is irradiated at 8 Gy and incubated for 48 hours. The other cell culture dish is shamed irradiated and considered as control (0 Gy).

Western Blot Analyses:

T lymphocytes proteins are extracted by RIPA buffer from two third of the cells (one third can be stored for complementary studies). Cell lysates are quantitated using the BCA protein assay kit (ThermoFisherScientific, Rockford, Ill.) according to the manufacturer's protocol. Ten micrograms of proteins are then loaded and separated on 12% SDS-PAGE and then transferred to a PVDF membrane. Nonspecific binding to the membrane is blocked for 1 hour at room temperature with 5% nonfat milk. Membranes are incubated overnight at 4° C. with the primary antibodies diluted as follows: AK2 (1/100, sc-28786; Santa Cruz Biotechnology, Inc., Santa Cruz Calif.), Annexin-1 (1/100, sc-11387; Santa Cruz Biotechnology, Inc., Santa Cruz Calif.), HSC70 (1/200, sc-7298; Santa Cruz Biotechnology, Inc., Santa Cruz Calif.), IDH2 (1/100, sc-134923; Santa Cruz Biotechnology, Inc., Santa Cruz Calif.) and Ref-1 (1/200, sc-5572; Santa Cruz Biotechnology, Inc., Santa Cruz Calif.). Membranes are then incubated with secondary antibody (goat anti-rabbit IgG (H+L), G21234; Invitrogen for AK2, Annexin-1, IDH2, Ref-1 and goat anti-mouse IgG (H+L), 115-035-146; Jackson ImmunoResearch for HSC70) for 1 hour at room temperature. The immunoblots are developed using the enhanced chemiluminescence detection system with the use of a SuperSignal West Pico Chemiluminescent Substrate kit (Pierce). Image analyses are performed using ImageJ software (National Institutes of Health, Bethesda, Md.).

Development of an ELISA Assay for the Five Candidate Proteins:

In order to propose a reliable, rapid and easy to use assay, an ELISA strategy is developed. Two antibodies are produced for each protein by Abnova against antigenic peptides. Said antibodies are already tested for ELISA. A sandwich-ELISA test is established in a 96-well format, using the antigen used for antibody production. The latter also serves as quantification standard. For each protein, one antibody serves to capture the target and is used to coat the wells. The other antibody is linked to biotin with the EZ-Link Sulfo-NHS-Biotinylation Kit from Pierce. Streptavidin-HRP together with an appropriate substrate buffer is used for detection. Concentration of the five candidate proteins is measured in the cell extracts obtained above with this test.

Figure 4:
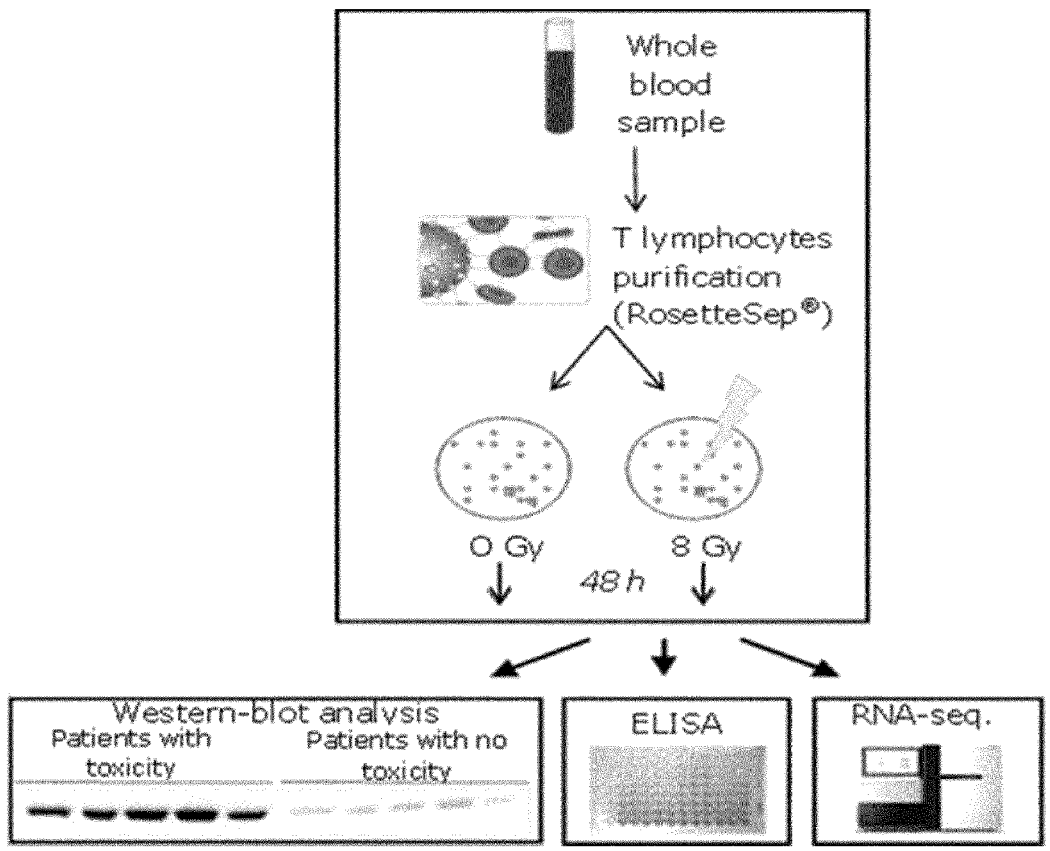
FIG. 4: Schematic representation of the test protocol for detecting the presence of the biomarkers

A protocol for protein analysis is represented in FIG. 4, and comprises the assessment of at least one, and preferably all of the following steps: western blot analysis, ELISA and RNA sequencing, on at least one and preferably at least a combination of two, three, four or five of the identified protein markers. One third of the cells (2.5 to 5 million cells per patient) obtained above, from patients presenting late toxicity and matched donors serve to extract RNA with Trizol reagent. The best experiment to measure transcriptional responses genome wide is global run on sequencing. A transcriptomic analysis through RNA sequencing (RNAseq) can be performed, with an alternative test being microarrays, even if this last technique is less sensitive. Importantly, RNAseq allows detection of alternative spliced transcripts as well as SNPs.

Example 5: Confirmation of the Predictive Role of the Proteins Identified

Figure 5A:
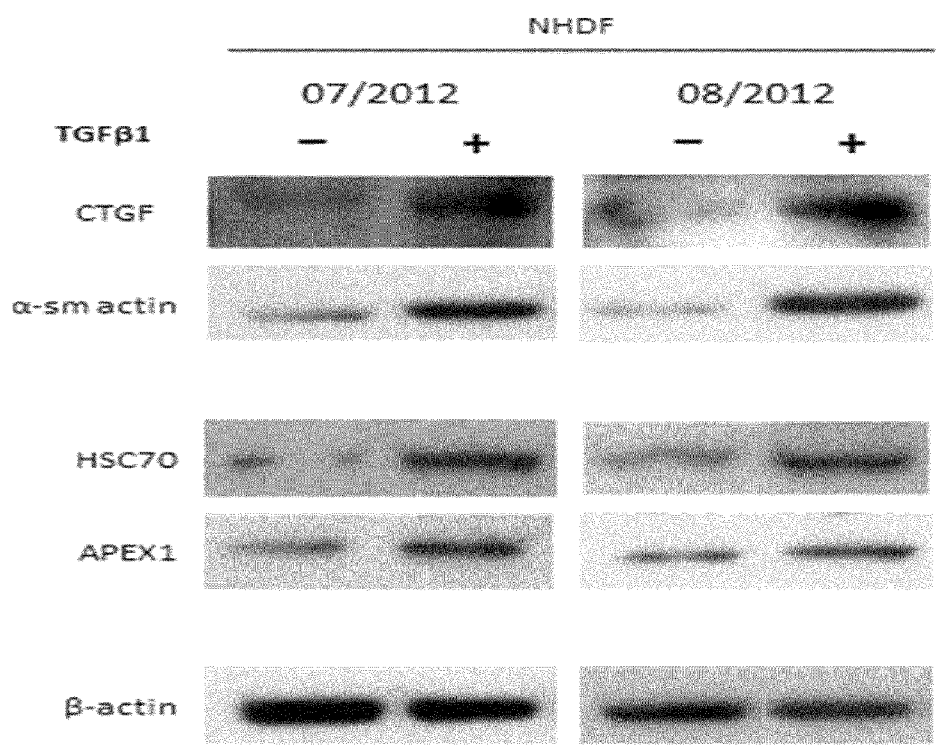
FIGS. 5A and 5B: Protein detection in induced fibrosis
Figure 5B:
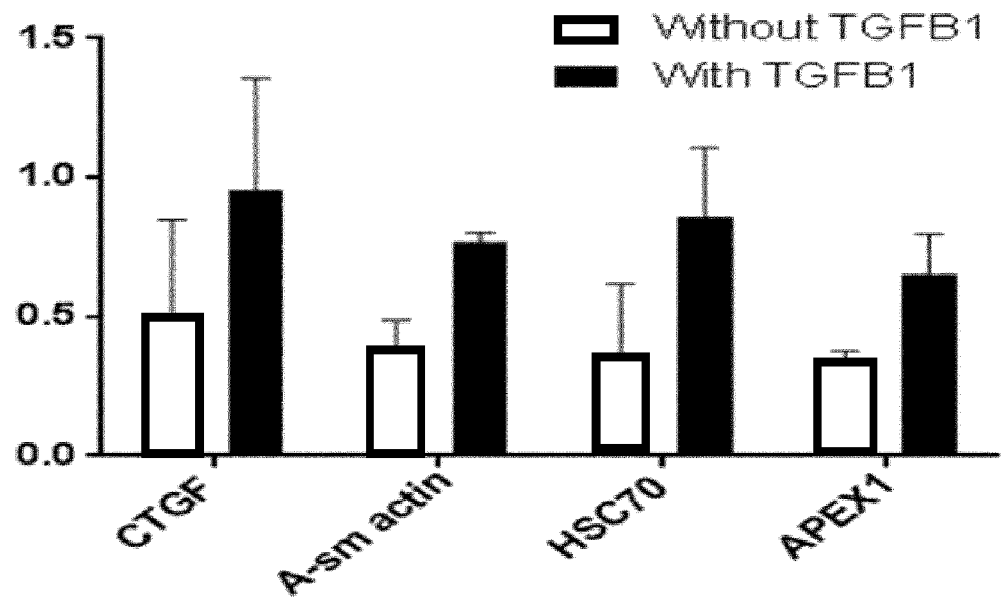

To confirm the predictive role of the 5 proteins (AK2, IDH2, ANX1, APEX1 and HSC70) in radiation-induced late side effects in terms of grade ≥2 subcutaneous fibrosis after breast-conserving surgery for a localized breast cancer and curative intent adjuvant radiotherapy as standard guideline. All blood samples are taken before radiotherapy. The induction of the transcription of AK2, IDH2, ANX1, APEX1 and HSC70 upon ionizing irradiation is studied. The expression of AK2, IDH2, ANX1, APEX1 and HSC70 after induction with TgFb1 is studied in fibroblasts and in human smooth interstitial muscle fibers (FIGS. 5A and 5B).

BIBLIOGRAPHIC REFERENCES

West C M et al., *Int. J. Radiat. Biol.*, 68, 197-203 (1995)
Floyd and Cassoni, *Eur. J. Cancer*, 30A, 615-20 (1994)
Ozsahin M et al., *Int. J. Radiat. Oncol. Biol. Phys.*, 38, 429-40 (1997)
Ozsahin M et al., *Clin. Cancer Res.*, 11, 7426-33 (2005)
Azria D et al., *Clin Cancer Res*, 14(19), 6284-6288 (2008)
Azria D et al., *Int. J. Radiat. Oncol. Biol. Phys.*, November (15), 75(4), 1275 (2009)
Azria D et al., *Crit. Rev. Oncol. Hematol.*, December, 84, suppl e35-41, (2012)
Guipaud O et al., *Proteomics*, 7, 3992-4002 (2007)
Cai X W et al., *Int J Radiat Oncol Biol Phys*, 77, 867-76 (2010)
Cai X W et al., *J Thorac Oncol*, 6, 1073-8 (2011)
Skvortdova et al., *Proteomics*, 4521-4533 (2008)
Stenmark et al., *Int. J Radiation Oncol Biol Phys*, 84(2), e217-222
Oh J H et al., *J Proteome Res*, 10, 1406-15 (2011)
Lacombe J et al., *Cancer/Radiotherapie*, 62-69 (2013)
Lee S H et al., *Int. J. Radiat. Biol*, 80(9), 635-42 (2004)
Someya S et al., *Cell*, 143(5), 802-12 (2010)
Lee J H et al., *J. Biol. Chem*, 282(18), 13385-94 (2007)
Tell G et al., *Antioxid Redox Signal*, 11(3), 601-20 (2009)
Yin M et al., *Int. J. Radiat. Oncol. Biol. Phys*, 81(3), 67-73 (2011)
Chang-Claude J et al., *Clin. Cancer Res*, 11(13), 4802-9 (2005)
Liu T et al., *Pharmacol Ther*, 136(3), 354-74 (2012)
Chong K Y et al., *J Mol Cell Cardiol* 30, 599-608 (1998)
Chen F et al., *Arterioscler Thromb Vasc Biol*, 32(12), 2989-99 (2012)

Burkart A et al., *J Biol. Chem,* 286(6), 4081-89 (2011)
Lim L H K et al., *FASEB Journal,* 21, 968-75 (2007)
Kennedy D R, Beerman T A. *Biochemistry* 45(11):3747-54 (2006)
Adema A D et al., *Int. J. Radiot. Biol,* 79(8), 655-66 (2003).

Cloos J et al., *Mutagenesis,* 14(1), 87-93 (1999).
Tedeschi B et al., *Mutation Research,* 546, 55-64 (2004)
Maniatis T. et al., *Molecular cloning, a Laboratory Manual,* Cold Spring Harbor Laboratory, Cold Spring Harbor, N.Y., Edition 1999

The invention claimed is:

1. A method for the in vitro determination of the radiosensitivity of a subject, comprising the steps of:
   a) inducing an exogenous stress by irradiation on a biological test sample comprising cells from said subject, wherein said irradiation is at a dose between 0.1 and 16 Gy, preferably between 2 and 14 Gy, more preferably is greater than 4 Gy, and more preferably is 8 Gy,
   b) determining in the sample of step a) the presence or level of a Heat shock cognate protein 71 kDa (HSC70),
   c) comparing the presence or level of HSC70 with the presence or level of the HSC70 in a reference sample, and
   d) determining, from the comparison of step c), the radiosensitivity of said subject.

2. The method of claim 1, wherein said biological sample is selected from the group consisting of whole blood extract containing lymphocytes and whole blood extract containing T lymphocytes.

3. The method of claim 1, wherein said biological sample is prepared by a process comprising the steps of:
   a) isolating lymphocytes from a whole blood extract,
   b) irradiating said isolated lymphocytes of step a), and
   c) extracting proteins from the lymphocytes of step b).

4. The method according to claim 1, wherein the presence or level of HSC70 is determined by a method comprising immuno-detection, western blot, mass spectrometry, chromatography, or flow cytometry.

5. The method of claim 1, further comprising:
   determining in the sample of step a) the presence or level of least one compound selected from the group consisting of a mitochondrial isocitrate dehydrogenase 2 (IDH2), a DNA-(apurinic or apyrimidinic site) lyase (APEX1), an adenylate kinase (AK2), an annexin 1 (ANX1), or a specific fragment thereof, or a nucleic acid encoding a Heat shock cognate protein 71 kDa (HSC70), a mitochondrial isocitrate dehydrogenase 2 (IDH2), a DNA-(apurinic or apyrimidinic site) lyase (APEX1), an adenylate kinase (AK2), an annexin 1 (ANX1), or a specific fragment thereof, or a combination thereof,
   comparing the presence or level of said at least one compound with the presence or level of the same compound in a reference sample, and
   determining, from the comparison the radiosensitivity of said subject.

6. The method according to claim 5, wherein the presence or level of a mitochondrial isocitrate dehydrogenase 2 (IDH2), a DNA-(apurinic or apyrimidinic site) lyase (APEX1), an adenylate kinase (AK2), and/or an annexin 1 (ANX1) is the determined by a method comprising immuno-detection, western blot, mass spectrometry, chromatography, or flow cytometry, and the nucleic acid encoding a Heat shock cognate protein 71 kDa (HSC70), a mitochondrial isocitrate dehydrogenase 2 (IDH2), a DNA-(apurinic or apyrimidinic site) lyase (APEX1), an adenylate kinase (AK2), an annexin 1 (ANX1), or a specific fragment thereof, is determined by a method for the specific detection of the presence or level of a nucleic acid.

7. The method according to claim 1, said method comprising additionally the steps of:
   e) inducing an exogenous stress by irradiation on a biological test sample comprising lymphocytes from said subject, f) determining the level of induced apoptosis in said biological test sample, and g) determining, from the determination of the level of induced apoptosis of step f) and from the comparison of step c) the radiosensitivity of said subject.

8. The method according to claim 1, wherein said subject is affected by a disease susceptible to be treated by radiotherapy, including cancer, disease of Basedow, pituitary adenome, meningiome or talalgy.

9. A method for predicting the susceptibility of late radio-induced toxicity in a subject, comprising the steps of:
   a) inducing an exogenous stress by irradiation on a biological test sample comprising cells from said subject, wherein said irradiation is at a dose between 0.1 and 16 Gy, preferably between 2 and 14 Gy, more preferably is greater than 4 Gy, and more preferably is 8 Gy,
   b) determining in the sample of step a) the presence or level of a Heat shock cognate protein 71 kDa (HSC70),
   c) comparing the presence or level of said HSC70 with the presence or level of HSC70 in a reference sample, and
   d) predicting the susceptibility to late radio-induced toxicity of said subject if HSC70 is present in said biological test sample and absent in said reference sample and/or if the level of said HSC70 in said biological test sample is superior to the level of the HSC70 in said reference sample.

10. The method of claim 9, further comprising:

determining in the sample of step a) the presence or level of least one compound selected from the group consisting of a mitochondrial isocitrate dehydrogenase 2 (IDH2), a DNA-(apurinic or apyrimidinic site) lyase (APEX1), an adenylate kinase (AK2), an annexin 1 (ANX1), or a specific fragment thereof, or a nucleic acid encoding a Heat shock cognate protein 71 kDa (HSC70), a mitochondrial isocitrate dehydrogenase 2 (IDH2), a DNA-(apurinic or apyrimidinic site) lyase (APEX1), an adenylate kinase (AK2), an annexin 1 (ANX1), or a specific fragment thereof, or a combination thereof, comparing the presence or level of said at least one compound with the presence or level of the same compound in a reference sample, and predicting the susceptibility to late radio-induced toxicity of said subject if said at least one compound is present in said biological test sample and absent in said reference sample and/or if the level of said at least one compound in said biological test sample is superior to the level of said at least one compound in said reference sample.

* * * * *

SEQUENCE LISTING

```
<160> NUMBER OF SEQ ID NOS: 10

<210> SEQ ID NO 1
<211> LENGTH: 452
<212> TYPE: PRT
<213> ORGANISM: Homo sapiens

<400> SEQUENCE: 1

Met Ala Gly Tyr Leu Arg Val Val Arg Ser Leu Cys Arg Ala Ser Gly
 1               5                  10                  15

Ser Arg Pro Ala Trp Ala Pro Ala Ala Leu Thr Ala Pro Thr Ser Gln
            20                  25                  30

Glu Gln Pro Arg Arg His Tyr Ala Asp Lys Arg Ile Lys Val Ala Lys
        35                  40                  45

Pro Val Val Glu Met Asp Gly Asp Glu Met Thr Arg Ile Ile Trp Gln
 50                  55                  60

Phe Ile Lys Glu Lys Leu Ile Leu Pro His Val Asp Ile Gln Leu Lys
 65                  70                  75                  80

Tyr Phe Asp Leu Gly Leu Pro Asn Arg Asp Gln Thr Asp Asp Gln Val
                85                  90                  95

Thr Ile Asp Ser Ala Leu Ala Thr Gln Lys Tyr Ser Val Ala Val Lys
            100                 105                 110

Cys Ala Thr Ile Thr Pro Asp Glu Ala Arg Val Glu Glu Phe Lys Leu
        115                 120                 125

Lys Lys Met Trp Lys Ser Pro Asn Gly Thr Ile Arg Asn Ile Leu Gly
130                 135                 140

Gly Thr Val Phe Arg Glu Pro Ile Ile Cys Lys Asn Ile Pro Arg Leu
145                 150                 155                 160

Val Pro Gly Trp Thr Lys Pro Ile Thr Ile Gly Arg His Ala His Gly
                165                 170                 175

Asp Gln Tyr Lys Ala Thr Asp Phe Val Ala Asp Arg Ala Gly Thr Phe
            180                 185                 190

Lys Met Val Phe Thr Pro Lys Asp Gly Ser Gly Val Lys Glu Trp Glu
        195                 200                 205

Val Tyr Asn Phe Pro Ala Gly Gly Val Gly Met Gly Met Tyr Asn Thr
    210                 215                 220

Asp Glu Ser Ile Ser Gly Phe Ala His Ser Cys Phe Gln Tyr Ala Ile
225                 230                 235                 240

Gln Lys Lys Trp Pro Leu Tyr Met Ser Thr Lys Asn Thr Ile Leu Lys
                245                 250                 255

Ala Tyr Asp Gly Arg Phe Lys Asp Ile Phe Gln Glu Ile Phe Asp Lys
            260                 265                 270

His Tyr Lys Thr Asp Phe Asp Lys Asn Lys Ile Trp Tyr Glu His Arg
        275                 280                 285

Leu Ile Asp Asp Met Val Ala Gln Val Leu Lys Ser Ser Gly Gly Phe
    290                 295                 300

Val Trp Ala Cys Lys Asn Tyr Asp Gly Asp Val Gln Ser Asp Ile Leu
305                 310                 315                 320

Ala Gln Gly Phe Gly Ser Leu Gly Leu Met Thr Ser Val Leu Val Cys
                325                 330                 335
```

```
Pro Asp Gly Lys Thr Ile Glu Ala Glu Ala His Gly Thr Val Thr
            340                 345                 350

Arg His Tyr Arg Glu His Gln Lys Gly Arg Pro Thr Ser Thr Asn Pro
        355                 360                 365

Ile Ala Ser Ile Phe Ala Trp Thr Arg Gly Leu Glu His Arg Gly Lys
370                 375                 380

Leu Asp Gly Asn Gln Asp Leu Ile Arg Phe Ala Gln Met Leu Glu Lys
385                 390                 395                 400

Val Cys Val Glu Thr Val Glu Ser Gly Ala Met Thr Lys Asp Leu Ala
                405                 410                 415

Gly Cys Ile His Gly Leu Ser Asn Val Lys Leu Asn Glu His Phe Leu
                420                 425                 430

Asn Thr Thr Asp Phe Leu Asp Thr Ile Lys Ser Asn Leu Asp Arg Ala
            435                 440                 445

Leu Gly Arg Gln
    450

<210> SEQ ID NO 2
<211> LENGTH: 318
<212> TYPE: PRT
<213> ORGANISM: Homo sapiens

<400> SEQUENCE: 2

Met Pro Lys Arg Gly Lys Lys Gly Ala Val Ala Glu Asp Gly Asp Glu
1               5                   10                  15

Leu Arg Thr Glu Pro Glu Ala Lys Lys Ser Lys Thr Ala Ala Lys Lys
            20                  25                  30

Asn Asp Lys Glu Ala Ala Gly Glu Gly Pro Ala Leu Tyr Glu Asp Pro
        35                  40                  45

Pro Asp Gln Lys Thr Ser Pro Ser Gly Lys Pro Ala Thr Leu Lys Ile
    50                  55                  60

Cys Ser Trp Asn Val Asp Gly Leu Arg Ala Trp Ile Lys Lys Lys Gly
65                  70                  75                  80

Leu Asp Trp Val Lys Glu Glu Ala Pro Asp Ile Leu Cys Leu Gln Glu
                85                  90                  95

Thr Lys Cys Ser Glu Asn Lys Leu Pro Ala Glu Leu Gln Glu Leu Pro
            100                 105                 110

Gly Leu Ser His Gln Tyr Trp Ser Ala Pro Ser Asp Lys Glu Gly Tyr
        115                 120                 125

Ser Gly Val Gly Leu Leu Ser Arg Gln Cys Pro Leu Lys Val Ser Tyr
    130                 135                 140

Gly Ile Gly Asp Glu Glu His Asp Gln Glu Gly Arg Val Ile Val Ala
145                 150                 155                 160

Glu Phe Asp Ser Phe Val Leu Val Thr Ala Tyr Val Pro Asn Ala Gly
                165                 170                 175

Arg Gly Leu Val Arg Leu Glu Tyr Arg Gln Arg Trp Asp Glu Ala Phe
            180                 185                 190

Arg Lys Phe Leu Lys Gly Leu Ala Ser Arg Lys Pro Leu Val Leu Cys
        195                 200                 205

Gly Asp Leu Asn Val Ala His Glu Glu Ile Asp Leu Arg Asn Pro Lys
    210                 215                 220

Gly Asn Lys Lys Asn Ala Gly Phe Thr Pro Gln Glu Arg Gln Gly Phe
225                 230                 235                 240

Gly Glu Leu Leu Gln Ala Val Pro Leu Ala Asp Ser Phe Arg His Leu
```

```
                    245                 250                 255
Tyr Pro Asn Thr Pro Tyr Ala Tyr Thr Phe Trp Thr Tyr Met Met Asn
                260                 265                 270

Ala Arg Ser Lys Asn Val Gly Trp Arg Leu Asp Tyr Phe Leu Leu Ser
            275                 280                 285

His Ser Leu Leu Pro Ala Leu Cys Asp Ser Lys Ile Arg Ser Lys Ala
        290                 295                 300

Leu Gly Ser Asp His Cys Pro Ile Thr Leu Tyr Leu Ala Leu
305                 310                 315

<210> SEQ ID NO 3
<211> LENGTH: 646
<212> TYPE: PRT
<213> ORGANISM: Homo sapiens

<400> SEQUENCE: 3

Met Ser Lys Gly Pro Ala Val Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Met Asn Pro Thr
        50                  55                  60

Asn Thr Val Phe Asp Ala Lys Arg Leu Ile Gly Arg Arg Phe Asp Asp
65                  70                  75                  80

Ala Val Val Gln Ser Asp Met Lys His Trp Pro Phe Met Val Val Asn
                85                  90                  95

Asp Ala Gly Arg Pro Lys Val Gln Val Glu Tyr Lys Gly Glu Thr Lys
            100                 105                 110

Ser Phe Tyr Pro Glu Glu Val Ser Ser Met Val Leu Thr Lys Met Lys
        115                 120                 125

Glu Ile Ala Glu Ala Tyr Leu Gly Lys Thr Val Thr Asn Ala Val Val
    130                 135                 140

Thr Val Pro Ala Tyr Phe Asn Asp Ser Gln Arg Gln Ala Thr Lys Asp
145                 150                 155                 160

Ala Gly Thr Ile Ala Gly Leu Asn Val Leu Arg Ile Ile Asn Glu Pro
                165                 170                 175

Thr Ala Ala Ala Ile Ala Tyr Gly Leu Asp Lys Lys Val Gly Ala Glu
            180                 185                 190

Arg Asn Val Leu Ile Phe Asp Leu Gly Gly Gly Thr Phe Asp Val Ser
        195                 200                 205

Ile Leu Thr Ile Glu Asp Gly Ile Phe Glu Val Lys Ser Thr Ala Gly
    210                 215                 220

Asp Thr His Leu Gly Gly Glu Asp Phe Asp Asn Arg Met Val Asn His
225                 230                 235                 240

Phe Ile Ala Glu Phe Lys Arg Lys His Lys Lys Asp Ile Ser Glu Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Ile Glu Ile Asp Ser Leu Tyr
        275                 280                 285

Glu Gly Ile Asp Phe Tyr Thr Ser Ile Thr Arg Ala Arg Phe Glu Glu
    290                 295                 300
```

```
Leu Asn Ala Asp Leu Phe Arg Gly Thr Leu Asp Pro Val Glu Lys Ala
305                 310                 315                 320

Leu Arg Asp Ala Lys Leu Asp Lys Ser Gln Ile His Asp Ile Val Leu
            325                 330                 335

Val Gly Gly Ser Thr Arg Ile Pro Lys Ile Gln Lys Leu Leu Gln Asp
        340                 345                 350

Phe Phe Asn Gly Lys Glu Leu Asn Lys Ser Ile Asn Pro Asp Glu Ala
        355                 360                 365

Val Ala Tyr Gly Ala Ala Val Gln Ala Ala Ile Leu Ser Gly Asp Lys
    370                 375                 380

Ser Glu Asn Val Gln Asp Leu Leu Leu Leu Asp Val Thr Pro Leu Ser
385                 390                 395                 400

Leu Gly Ile Glu Thr Ala Gly Gly Val Met Thr Val Leu Ile Lys Arg
            405                 410                 415

Asn Thr Thr Ile Pro Thr Lys Gln Thr Gln Thr Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Lys Phe Glu Leu Thr Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Ser Ala Val Asp Lys Ser Thr Gly
                485                 490                 495

Lys Glu Asn Lys Ile Thr Ile Thr Asn Asp Lys Gly Arg Leu Ser Lys
            500                 505                 510

Glu Asp Ile Glu Arg Met Val Gln Glu Ala Glu Lys Tyr Lys Ala Glu
        515                 520                 525

Asp Glu Lys Gln Arg Asp Lys Val Ser Ser Lys Asn Ser Leu Glu Ser
    530                 535                 540

Tyr Ala Phe Asn Met Lys Ala Thr Val Glu Asp Glu Lys Leu Gln Gly
545                 550                 555                 560

Lys Ile Asn Asp Glu Asp Lys Gln Lys Ile Leu Asp Lys Cys Asn Glu
                565                 570                 575

Ile Ile Asn Trp Leu Asp Lys Asn Gln Thr Ala Glu Lys Glu Glu Phe
            580                 585                 590

Glu His Gln Gln Lys Glu Leu Glu Lys Val Cys Asn Pro Ile Ile Thr
        595                 600                 605

Lys Leu Tyr Gln Ser Ala Gly Gly Met Pro Gly Gly Met Pro Gly Gly
    610                 615                 620

Phe Pro Gly Gly Gly Ala Pro Pro Ser Gly Gly Ala Ser Ser Gly Pro
625                 630                 635                 640

Thr Ile Glu Glu Val Asp
                645

<210> SEQ ID NO 4
<211> LENGTH: 239
<212> TYPE: PRT
<213> ORGANISM: Homo sapiens

<400> SEQUENCE: 4

Met Ala Pro Ser Val Pro Ala Ala Glu Pro Glu Tyr Pro Lys Gly Ile
1               5                   10                  15

Arg Ala Val Leu Leu Gly Pro Pro Gly Ala Gly Lys Gly Thr Gln Ala
            20                  25                  30
```

Pro Arg Leu Ala Glu Asn Phe Cys Val Cys His Leu Ala Thr Gly Asp
            35                  40                  45

Met Leu Arg Ala Met Val Ala Ser Gly Ser Glu Leu Gly Lys Lys Leu
 50                  55                  60

Lys Ala Thr Met Asp Ala Gly Lys Leu Val Ser Asp Glu Met Val Val
 65                  70                  75                  80

Glu Leu Ile Glu Lys Asn Leu Glu Thr Pro Leu Cys Lys Asn Gly Phe
                85                  90                  95

Leu Leu Asp Gly Phe Pro Arg Thr Val Arg Gln Ala Glu Met Leu Asp
            100                 105                 110

Asp Leu Met Glu Lys Arg Lys Glu Lys Leu Asp Ser Val Ile Glu Phe
            115                 120                 125

Ser Ile Pro Asp Ser Leu Leu Ile Arg Arg Ile Thr Gly Arg Leu Ile
130                 135                 140

His Pro Lys Ser Gly Arg Ser Tyr His Glu Glu Phe Asn Pro Pro Lys
145                 150                 155                 160

Glu Pro Met Lys Asp Asp Ile Thr Gly Glu Pro Leu Ile Arg Arg Ser
                165                 170                 175

Asp Asp Asn Glu Lys Ala Leu Lys Ile Arg Leu Gln Ala Tyr His Thr
            180                 185                 190

Gln Thr Thr Pro Leu Ile Glu Tyr Tyr Arg Lys Arg Gly Ile His Ser
            195                 200                 205

Ala Ile Asp Ala Ser Gln Thr Pro Asp Val Val Phe Ala Ser Ile Leu
210                 215                 220

Ala Ala Phe Ser Lys Ala Thr Cys Lys Asp Leu Val Met Phe Ile
225                 230                 235

<210> SEQ ID NO 5
<211> LENGTH: 346
<212> TYPE: PRT
<213> ORGANISM: Homo sapiens

<400> SEQUENCE: 5

Met Ala Met Val Ser Glu Phe Leu Lys Gln Ala Trp Phe Ile Glu Asn
 1               5                  10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
 50                  55                  60

Ile Ile Asp Ile Leu Thr Lys Arg Asn Asn Ala Gln Arg Gln Gln Ile
 65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
            115                 120                 125

Gly Leu Gly Thr Asp Glu Asp Thr Leu Ile Glu Ile Leu Ala Ser Arg
            130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe 165                 170                 175
Arg Asn Ala Leu Leu Ser Leu Ala Lys Gly Asp Arg Ser Glu Asp Phe
                180                 185                 190

Gly Val Asn Glu Asp Leu Ala Asp Ser Asp Ala Arg Ala Leu Tyr Glu
            195                 200                 205

Ala Gly Glu Arg Arg Lys Gly Thr Asp Val Asn Val Phe Asn Thr Ile
        210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 6
<211> LENGTH: 1740
<212> TYPE: DNA
<213> ORGANISM: Homo sapiens

<400> SEQUENCE: 6
ccagcgttag cccgcggcca ggcagccggg aggagcggcg cgcgctcgga cctctcccgc      60
cctgctcgtt cgctctccag cttgggatgg ccggctacct gcgggtcgtg cgctcgctct     120
gcagagcctc aggctcgcgg ccggcctggg cgccggcggc cctgacagcc cccacctcgc     180
aagagcagcc gcggcgccac tatgccgaca aaaggatcaa ggtggcgaag cccgtggtgg     240
agatggatgg tgatgagatg acccgtatta tctggcagtt catcaaggag aagctcatcc     300
tgccccacgt ggacatccag ctaaagtatt ttgacctcgg gctcccaaac cgtgaccaga     360
ctgatgacca ggtcaccatt gactctgcac tggccaccca gaagtacagt gtggctgtca     420
agtgtgccac catcaccccct gatgaggccc gtgtggaaga gttcaagctg aagaagatgt     480
ggaaaagtcc caatggaact atccggaaca tcctgggggg gactgtcttc cgggagccca     540
tcatctgcaa aaacatccca cgcctagtcc ctggctggac caagcccatc accattggca     600
ggcacgccca tggcgaccag tacaaggcca cagactttgt ggcagaccgg ccggcacttt     660
tcaaaatggt cttcacccca aaagatggca gtggtgtcaa ggagtgggaa gtgtacaact     720
tccccgcagg cggcgtgggc atgggcatgt acaacaccga cgagtccatc tcaggttttg     780
cgcacagctg cttccagtat gccatccaga agaaatggcc gctgtacatg agcaccaaga     840
acaccatact gaaagcctac gatgggcgtt tcaaggacat cttccaggag atctttgaca     900
agcactataa gaccgacttc gacaagaata gatctggta tgagcaccgg ctcattgatg     960
acatggtggc tcaggtcctc aagtcttcgg gtggctttgt gtgggcctgc aagaactatg    1020
acggagatgt gcagtcagac atcctggccc agggctttgg ctcccttggc ctgatgacgt    1080

| | |
|---|---:|
| ccgtcctggt ctgccctgat gggaagacga ttgaggctga ggccgctcat gggaccgtca | 1140 |
| cccgccacta tcgggagcac cagaagggcc ggcccaccag caccaacccc atcgccagca | 1200 |
| tctttgcctg gacacgtggc ctggagcacc gggggaagct ggatgggaac caagacctca | 1260 |
| tcaggtttgc ccagatgctg gagaaggtgt gcgtggagac ggtggagagt ggagccatga | 1320 |
| ccaaggacct ggcgggctgc attcacggcc tcagcaatgt gaagctgaac gagcacttcc | 1380 |
| tgaacaccac ggacttcctc gacaccatca gagcaacct ggacagagcc ctgggcaggc | 1440 |
| agtaggggga ggcgccaccc atggctgcag tggaggggcc agggctgagc cggcgggtcc | 1500 |
| tcctgagcgc ggcagagggt gagcctcaca gcccctctct ggaggccttt ctaggggatg | 1560 |
| ttttttttata agccagatgt ttttaaaagc atatgtgtgt ttcccctcat ggtgacgtga | 1620 |
| ggcaggagca gtgcgtttta cctcagccag tcagtatgtt ttgcatactg taatttatat | 1680 |
| tgcccttgga acacatggtg ccatatttag ctactaaaaa gctcttcaca aaaaaaaaaa | 1740 |

<210> SEQ ID NO 7
<211> LENGTH: 1558
<212> TYPE: DNA
<213> ORGANISM: Homo sapiens

<400> SEQUENCE: 7

| | |
|---|---:|
| cagacagacc aatcacgcgc attcttcggc cacgacaagc gcgcctctga tcacgtgacc | 60 |
| aggtccgcta cccacgtggg ggctcagcgt gcacccttct ttgtgctcgg gttaggagga | 120 |
| gctaggctgc catcgggccg gtgcagatac ggggttgctc ttttgctcat aagaggggct | 180 |
| tcgctggcag tctgaacggc aagcttgagt caggacccctt aattaagatc ctcaattggc | 240 |
| tggagggcag atctcgcgag caacgcggta aaaatattgc ttcggtgggt gacgcggtac | 300 |
| agctgcccaa gggcgttcgt aacgggaatg ccgaagcgtg ggaaaaaggg agcggtggcg | 360 |
| gaagacgggg atgagctcag gacagagcca gaggccaaga agagtaagac ggccgcaaag | 420 |
| aaaaatgaca agaggcagc aggagagggc ccagccctgt atgaggaccc ccagatcag | 480 |
| aaaacctcac ccagtggcaa acctgccaca ctcaagatct gctcttggaa tgtggatggg | 540 |
| cttcgagcct ggattaagaa gaaaggatta gattgggtaa aggaagaagc cccagatata | 600 |
| ctgtgccttc aagagaccaa atgttcagag aacaaactac cagctgaact tcaggagctg | 660 |
| cctggactct ctcatcaata ctggtcagct ccttcggaca aggaagggta cagtggcgtg | 720 |
| ggcctgcttt cccgccagtg cccactcaaa gtttcttacg gcataggcga tgaggagcat | 780 |
| gatcaggaag gccgggtgat tgtggctgaa tttgactcgt ttgtgctggt aacagcatat | 840 |
| gtacctaatg caggccgagg tctggtacga ctggagtacc ggcagcgctg ggatgaagcc | 900 |
| tttcgcaagt tcctgaaggg cctggcttcc cgaaagcccc ttgtgctgtg tggagacctc | 960 |
| aatgtggcac atgaagaaat tgaccttcgc aaccccaagg ggaacaaaaa gaatgctggc | 1020 |
| ttcacgccac aagagcgcca aggcttcggg gaattactgc aggctgtgcc actggctgac | 1080 |
| agctttaggc acctctaccc caacacaccc tatgcctaca ccttttggac ttatatgatg | 1140 |
| aatgctcgat ccaagaatgt tggttggcgc cttgattact tttgttgtc ccactctctg | 1200 |
| ttacctgcat tgtgtgacag caagatccgt tccaaggccc tcgcagtga tcactgtcct | 1260 |
| atcaccctat acctagcact gtgacaccac ccctaaatca ctttgagcct gggaaataag | 1320 |
| cccccctcaac taccattcct tctttaaaca ctcttcagag aaatctgcat tctatttctc | 1380 |
| atgtataaaa ctaggaatcc tccaaccagg ctcctgtgat agagttcttt taagcccaag | 1440 |
| attttttatt tgagggtttt ttgttttttta aaaaaaaatt gaacaaagac tactaatgac | 1500 |

```
tttgtttgaa ttatccacat gaaaataaag agccatagtt tcagccttaa aaaaaaaa      1558
```

<210> SEQ ID NO 8
<211> LENGTH: 2331
<212> TYPE: DNA
<213> ORGANISM: Homo sapiens

<400> SEQUENCE: 8

```
ccttctggaa ggttctaaga tagggtataa gaggcagggt ggcgggcgga aaccggtctc      60
attgaactcg cctgcagctc ttgggttttt tgtggcttcc ttcgttattg gagccaggcc     120
tacaccccag caaccatgtc caagggacct gcagttggta ttgatcttgg caccacctac     180
tcttgtgtgg gtgttttcca gcacggaaaa gtcgagataa ttgccaatga tcagggaaac     240
cgaaccactc caagctatgt cgcctttacg gacactgaac ggttgatcgg tgatgccgca     300
aagaatcaag ttgcaatgaa ccccaccaac acagttttg atgccaaacg tctgattgga     360
cgcagatttg atgatgctgt tgtccagtct gatatgaaac attggccctt tatggtggtg     420
aatgatgctg gcaggcccaa ggtccaagta gaatacaagg gagagaccaa aagcttctat     480
ccagaggagt gtcttctat ggttctgaca aagatgaagg aaattgcaga agcctacctt     540
gggaagactg ttaccaatgc tgtggtcaca gtgccagctt actttaatga ctctcagcgt     600
caggctacca aagatgctgg aactattgct ggtctcaatg tacttagaat tattaatgag     660
ccaactgctg ctgctattgc ttacggctta gacaaaaagg ttggagcaga agaaacgtg     720
ctcatctttg acctgggagg tggcactttt gatgtgtcaa tcctcactat tgaggatgga     780
atctttgagg tcaagtctac agctggagac acccacttgg gtggagaaga ttttgacaac     840
cgaatggtca accatttat tgctgagttt aagcgcaagc ataagaagga catcagtgag     900
aacaagagag ctgtaagacg cctccgtact gcttgtgaac gtgctaagcg taccctctct     960
tccagcaccc aggccagtat tgagatcgat tctctctatg aaggaatcga cttctatacc     1020
tccattaccc gtgcccgatt tgaagaactg aatgctgacc tgttccgtgg cacccctggac     1080
ccagtagaga aagcccttcg agatgccaaa ctagacaagt cacagattca tgatattgtc     1140
ctggttggtg gttctactcg tatccccaag attcagaagc ttctccaaga cttcttcaat     1200
ggaaaagaac tgaataagag catcaacccct gatgaagctg ttgcttatgg tgcagctgtc     1260
caggcagcca tcttgtctgg agacaagtct gagaatgttc aagatttgct gctcttggat     1320
gtcactcctc tttcccttgg tattgaaact gctggtggag tcatgactgt cctcatcaag     1380
cgtaatacca ccattcctac caagcagaca cagaccttca ctacctattc tgacaaccag     1440
cctggtgtgc ttattcaggt ttatgaaggc gagcgtgcca tgacaaagga taacaacctg     1500
cttggcaagt tgaactcac aggcatacct cctgcacccc gaggtgttcc tcagattgaa     1560
gtcactttg acattgatgc caatggtata ctcaatgtct ctgctgtgga caagagtacg     1620
ggaaaagaga acaagattac tatcactaat gacaagggcc gttttgagcaa ggaagacatt     1680
gaacgtatgg tccaggaagc tgagaagtac aaagctgaag atgagaagca gagggacaag     1740
gtgtcatcca agaattcact tgagtcctat gccttcaaca tgaaagcaac tgttgaagat     1800
gagaaacttc aaggcaagat taacgatgag gacaaacaga gattctgga caagtgtaat     1860
gaaattatca actggcttga taagaatcag actgctgaga aggaagaatt tgaacatcaa     1920
cagaaagagc tggagaaagt ttgcaacccc atcatcacca agctgtacca gagtgcagga     1980
ggcatgccag gaggaatgcc tgggggattt cctggtggtg gagctcctcc ctctggtggt     2040
```

| | |
|---|---:|
| gcttcctcag ggcccaccat tgaagaggtt gattaagcca accaagtgta gatgtagcat | 2100 |
| tgttccacac atttaaaaca tttgaaggac ctaaattcgt agcaaattct gtggcagttt | 2160 |
| taaaaagtta agctgctata gtaagttact gggcattctc aatacttgaa tatggaacat | 2220 |
| atgcacaggg gaaggaaata acattgcact ttataaacac tgtattgtaa gtggaaaatg | 2280 |
| caatgtctta ataaaactaa tttaaaattg gcaccataaa aaaaaaaaaa a | 2331 |

<210> SEQ ID NO 9
<211> LENGTH: 3647
<212> TYPE: DNA
<213> ORGANISM: Homo sapiens

<400> SEQUENCE: 9

| | |
|---|---:|
| gtgcgtggcg tgcgtgcgtt gacctgggaa gcactggacc tgtgaggcgt gcgaactggt | 60 |
| ggcagtgaga gacttcggcg gacatggctc ccagcgtgcc agcggcagaa cccgagtatc | 120 |
| ctaaaggcat ccgggccgtg ctgctggggc ctcccggggc cggtaaaggg acccaggcac | 180 |
| ccagattggc tgaaaacttc tgtgtctgcc atttagctac tggggacatg ctgagggcca | 240 |
| tggtggcttc tggctcagag ctaggaaaaa agctgaaggc aactatggat gctgggaaac | 300 |
| tggtgagtga tgaaatggta gtggagctca ttgagaagaa tttggagacc ccttgtgca | 360 |
| aaaatggttt tcttctggat ggcttccctc ggactgtgag gcaggcagaa atgctcgatg | 420 |
| acctcatgga gaagagaaa gagaagcttg attctgtgat tgaattcagc atcccagact | 480 |
| ctctgctgat tcaccccaag agtggccgtt cctaccacga ggagttcaac cctccaaaag | 540 |
| agcccatgaa agatgacatc accggggaac ccttgatccg tcgatcagat gataatgaaa | 600 |
| aggccttgaa aatccgcctg caagcctacc acactcaaac caccccactc atagagtact | 660 |
| acaggaaacg ggggatccac tccgccatcg atgcatccca gaccccgat gtcgtgttcg | 720 |
| caagcatcct agcagccttc tccaaagcca catcctagta tcagaaggcc aggcgagact | 780 |
| gcaacactgc tcatcacccc gcggcgtgat ccctgctctt aggtgctggg cagaggggaa | 840 |
| gggtggtcag ggtgaggatg gtgagggagg gctggtgagg ggctcagagg aatacttgga | 900 |
| acaacagcag tgttattgta gtgtggcagt ttctttttata cataggtgag agttttaaa | 960 |
| gtgtaaggga aaaattaatt ttttaaaaaa caccatgctt ggagggtggg ggtagaaata | 1020 |
| gacacaatat tatttctaag gaatcgggtt ttcatttact ctggactggt gaaaatattt | 1080 |
| tttaaagcca gtgctctaag acctcagctt ttatctcaga accccatggg ttccagacca | 1140 |
| agagtacagg aaatcaaatt gttgtcctgt ctgtctatag cttggaacag ggagctttga | 1200 |
| ttactgactc cggttccaca cactgtaaga tcaaaaaacc atctccacat ttgaaagaga | 1260 |
| tgtaaggtgt attcataggg atggtggctc aacaaatcaa gcaaactgga atcaagggga | 1320 |
| ggggaaggg aatgaaatgg aaagggaggc tgattcccctt cccctgactt accactaatt | 1380 |
| tactaggcta cctactttca tgagtaacct ctcacagcta cccagcacat gccacaatcc | 1440 |
| tatgctcttg ccttctttta tctgcactgt gtgaagggac tctttaaat aaatgagcaa | 1500 |
| gtgtcctaag ctatgtcatc caaagattgt cctttccatt ctcaaatcct gtgactggga | 1560 |
| tcactcaaca gcactgtgat gtattatttt caatgaggtg cctttcttaa ctgaccaaat | 1620 |
| gctgccttgt ttggccccta aatcaataaa atatgttaaa atttgtatcc cctgttgtgg | 1680 |
| catttttttt agataatcta agctagaaaa atgacattga attctggacc tggctggaag | 1740 |
| gaaaagaagc ccttcttgt cgctggcagc tgtgtggtag ggaggtccaa gtatgtgcat | 1800 |
| atgagataag cctgcaacct cttgaccttc agctcctatg caggcttctc ttgagcccag | 1860 |

```
agacaaggca gcttggtcta gtggagatag cactgtgctt ggagttcagg ggacctagga    1920
caaatcccag ccagttagtt attcactgtg ctcctgtttc ctcagctgaa aaaggaagtt    1980
ggttatgcca ccttcttggc cttaatggca ttaaatgaaa tttataggaa gaaggttttt    2040
gctcagtacc tggcatgcaa cagacattgg ataaatgtta gttggatcca gatatacaca    2100
gaaagatatc tgcttcctgc caggctggat aactgttgaa tggacacttg tccatagtct    2160
agaaagccag tgcttctaat ccttaagcca gatctttgac tacctttca gttgcttctt    2220 taacactctt tgttgcttct ctgtgtgtcc tagtttaaat tcatttcctc tccagcaaaa    2280
gtgagcttaa ataatttctc caaactaaag ctctcatgtt tttggaaggg ctgcctttgc    2340
aagtgaggtt tctgagaaat gactgttgtt cccaaaacaa gagggagctg gctggaagc    2400 accactattc ttctttaggc atcttgttac agagagaggc agggtcttca ctgacatatt    2460
aaatcctgtt ccctgaacca gcccctccct cttctgctcc acttcctcac ctgtgcagag    2520
tcattttcag gtgttagcct tactgatttg cactgatctg tttgttccct gagctttta    2580 aatacccctgt gaaaattttc tttcctccct tggtcatcat gcatctaatt gtggggaaat    2640
gtttgtcaaa ccaacctgca aagcagcatg gtgtagttga aagaataaa cagagaagac    2700 tgggtgagct attgtttgtt tgcttctttg ggcctgggtt tcctcatcta atctgcaaac    2760
caagaatgca gactagtcct accactcccg gaagactgac gttgtgccag gtattatgca    2820
aaggcttcat gtaaccctcg acttcacgta accctcacac agcaccctgt ggagtcagaa    2880
ctgtccttca cttttatagg tgaggaaacc agactcagag aggtgaagtg gcattcctga    2940
ggtcatgcat aagaggcagt caggactgaa acacagtctc taacacttat ccgtcccctt    3000
gatcttgttg ctgaagtgat ttaattactt gcgtagctct gcacacagga agggctgctc    3060
tgaataagag ctcttttcca tggacactca gcgctgccgg aactgatttt gaagaagtca    3120
ctgccggctc tgagggccta gggtatgtgt cttaggatct cctgtgtgca caaagtgtca    3180
ctgacagaac acagcaggat ggagagcagc ctcctcagaa gcctcacaag tctttcctca    3240
gatgaagaca gagcaacgag tcagaagaca gatttcaaca gcgacttcac catgcgacct    3300
tggacaagtt atctcacctc atcagtagaa taggaatgat ccctacccct caaaggtgct    3360
gatgacacta gtgaccaaga tactcatgtg ggttggactg cccaggacac agcagatgct    3420
tagtaaacac agatggaatt cagagggaaa atgtaggcat tgaagaaagt tgtcttactg    3480
accatccgga accaggctaa ggatccccta gaaatcatag acctctgaaa ttatatgcag    3540
aattctttat gtgttttcat aattaataat agtctaacat attaaattct tagctgtgtg    3600
agaggttctg catgcattat ctcatttatt ctcctcgata accctgt                 3647
```

<210> SEQ ID NO 10
<211> LENGTH: 1399
<212> TYPE: DNA
<213> ORGANISM: Homo sapiens

<400> SEQUENCE: 10

```
agtgtgaaat cttcagagaa gaatttctct ttagttcttt gcaagaaggt agagataaag     60
acactttttc aaaaatggca atggtatcag aattcctcaa gcaggcctgg tttattgaaa    120
atgaagagca ggaatatgtt caaactgtga agtcatccaa aggtggtccc ggatcagcgg    180
tgagccccta tcctaccttc aatccatcct cggatgtcgc tgccttgcat aaggccataa    240
tggttaaagg tgtggatgaa gcaaccatca ttgacattct aactaagcga aacaatgcac    300
```

```
agcgtcaaca gatcaaagca gcatatctcc aggaaacagg aaagccctg gatgaaacac      360 ttaagaaagc ccttacaggt caccttgagg aggttgtttt agctctgcta aaaactccag      420
cgcaatttga tgctgatgaa cttcgtgctg ccatgaaggg ccttggaact gatgaagata      480
ctctaattga gattttggca tcaagaacta acaaagaaat cagagacatt aacagggtct      540
acagagagga actgaagaga gatctggcca aagacataac ctcagacaca tctggagatt      600
ttcggaacgc tttgctttct cttgctaagg gtgaccgatc tgaggacttt ggtgtgaatg      660
aagacttggc tgattcagat gccagggcct tgtatgaagc aggagaaagg agaaagggga      720
cagacgtaaa cgtgttcaat accatcctta ccaccagaag ctatccacaa cttcgcagag      780
tgtttcagaa atacaccaag tacagtaagc atgacatgaa caaagttctg gacctggagt      840 tgaaggtga cattgagaaa tgcctcacag ctatcgtgaa gtgcgccaca agcaaaccag       900
ctttctttgc agagaagctt catcaagcca tgaaaggtgt tggaactcgc cataaggcat      960
tgatcaggat tatggtttcc cgttctgaaa ttgacatgaa tgatatcaaa gcattctatc     1020
agaagatgta tggtatctcc ctttgccaag ccatcctgga tgaaaccaaa ggagattatg     1080
agaaaatcct ggtggctctt tgtggaggaa actaaacatt cccttgatgg tctcaagcta     1140
tgatcagaag actttaatta tatattttca tcctataagc ttaaatagga aagtttcttc     1200
aacaggatta cagtgtagct acctacatgc tgaaaaatat agcctttaaa tcattttat      1260 attataactc tgtataatag agataagtcc attttttaaa aatgttttcc ccaaaccata     1320
aaaccctata caagttgttc tagtaacaat acatgagaaa gatgtctatg tagctgaaaa     1380
taaaatgacg tcacaagac                                                  1399
```